US006749868B1

United States Patent
Desai et al.

(10) Patent No.: US 6,749,868 B1
(45) Date of Patent: *Jun. 15, 2004

(54) PROTEIN STABILIZED PHARMACOLOGICALLY ACTIVE AGENTS, METHODS FOR THE PREPARATION THEREOF AND METHODS FOR THE USE THEREOF

(75) Inventors: Neil P. Desai, Los Angeles, CA (US); Chunlin Tao, Beverly Hills, CA (US); Andrew Yang, Rosemead, CA (US); Leslie Louie, Montebello, CA (US); Zhiwen Yao, Culver City, CA (US); Patrick Soon-Shiong, Los Angeles, CA (US); Shlomo Magdassi, Jerusalem (IL)

(73) Assignee: American BioScience, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,642

(22) Filed: May 21, 1999

Related U.S. Application Data

(63) Continuation-in-part of application No. 09/198,082, filed on Nov. 23, 1998, now abandoned, which is a division of application No. 08/720,756, filed on Oct. 1, 1996, now Pat. No. 5,916,596, which is a continuation-in-part of application No. 08/412,726, filed on Mar. 29, 1995, now Pat. No. 5,560,933, which is a continuation-in-part of application No. 08/023,698, filed on Feb. 22, 1993.

(51) Int. Cl.[7] .............................. A61K 9/16; A61K 9/50
(52) U.S. Cl. ........................ 424/491; 424/489; 424/490
(58) Field of Search ................................ 424/491, 497, 424/499, 489, 490

(56) References Cited

U.S. PATENT DOCUMENTS 4,344,934 A    8/1982  Martin et al. .................. 424/80

(List continued on next page.)

FOREIGN PATENT DOCUMENTS

| EP | 0 123 456 A2 | 10/1984 |
| WO | WO 94/18954 | 9/1994 |

OTHER PUBLICATIONS

Physicians'Desk Reference (52 Ed. 1998).

Drug Facts and Comparisons (1999 Ed., pp. 3548–1558).

*Primary Examiner*—Thurman K. Page
*Assistant Examiner*—Liliana Di Nola-Baron
(74) *Attorney, Agent, or Firm*—Stephen E. Reiter; Foley & Lardner

(57) ABSTRACT

In accordance with the present invention, there are provided compositions and methods useful for the in vivo delivery of substantially water insoluble pharmacologically active agents (such as the anticancer drug paclitaxel) in which the pharmacologically active agent is delivered in the form of suspended particles coated with protein (which acts as a stabilizing agent). In particular, protein and pharmacologically active agent in a biocompatible dispersing medium are subjected to high shear, in the absence of any conventional surfactants, and also in the absence of any polymeric core material for the particles. The procedure yields particles with a diameter of less than about 1 micron. The use of specific composition and preparation conditions (e.g., addition of a polar solvent to the organic phase), and careful election of the proper organic phase and phase fraction, enables the reproducible production of unusually small nanoparticles of less than 200 nm diameter, which can be sterile-filtered. The particulate system produced according to the invention can be converted into a redispersible dry powder comprising nanoparticles of water-insoluble drug coated with a protein, and free protein to which molecules of the pharmacological agent are bound. This results in a unique delivery system, in which part of the pharmacologically active agent is readily bioavailable (in the form of molecules bound to the protein), and part of the agent is present within particles without any polymeric matrix therein.

21 Claims, 2 Drawing Sheets

U.S. PATENT DOCUMENTS

| | | | |
|---|---|---|---|
| 5,399,363 A | 3/1995 | Liversidge et al. | 424/490 |
| 5,439,686 A | 8/1995 | Desai et al. | |
| 5,498,421 A | 3/1996 | Grinstaff et al. | |
| 5,504,102 A | 4/1996 | Agharkar et al. | 514/449 |
| 5,543,152 A | 8/1996 | Webb et al. | 424/450 |
| 5,565,478 A | 10/1996 | Kohn et al. | 514/359 |
| 5,626,862 A | 5/1997 | Brem et al. | 424/426 |
| 5,637,625 A | 6/1997 | Haynes | |
| 5,648,090 A | 7/1997 | Rahman et al. | 424/450 |
| 5,683,715 A | 11/1997 | Boni et al. | 424/450 |
| 5,714,520 A | 2/1998 | Jones et al. | |
| 5,731,334 A | 3/1998 | Wrasidlo | 514/358 |
| 5,731,355 A | 3/1998 | Jones et al. | |
| 5,731,356 A | 3/1998 | Jones et al. | |
| 5,744,460 A | 4/1998 | Müller et al. | 514/44 |
| 5,908,869 A | 6/1999 | Jones et al. | |
| 5,916,596 A * | 6/1999 | Desai et al. | 424/489 |
| 5,962,536 A | 10/1999 | Komer | |
| 5,977,163 A | 11/1999 | Li et al. | 514/449 |
| 6,028,108 A | 2/2000 | George | |
| 6,096,331 A | 8/2000 | Desai et al. | 424/422 |
| 6,100,302 A | 8/2000 | Pejaver et al. | |
| 6,140,373 A | 10/2000 | May et al. | |
| 6,147,122 A | 11/2000 | Mirejovsky et al. | |
| 6,150,423 A | 11/2000 | Carpenter | |
| 6,177,477 B1 | 1/2001 | George et al. | |
| 6,326,406 B1 | 12/2001 | De Tommaso | |
| 6,362,234 B1 | 3/2002 | Hendler | |
| 6,399,087 B1 | 6/2002 | Zhang et al. | |
| 6,469,069 B1 | 10/2002 | Mirejovsky et al. | |
| 6,537,579 B1 * | 3/2003 | Desai et al. | 424/489 |

* cited by examiner

PROTEIN STABILIZED PHARMACOLOGICALLY ACTIVE AGENTS, METHODS FOR THE PREPARATION THEREOF AND METHODS FOR THE USE THEREOF

RELATED APPLICATIONS

This application is a continuation-in-part of U.S. Ser. No. 09/198,082, filed Nov. 23, 1998, now abandoned, which is a divisional of U.S. Ser. No. 08/720,756, filed on Oct. 1, 1996, now U.S. Pat. No. 5,916,596, which is a continuation-in-part of U.S. Ser. No. 08/412,726, filed Mar. 29, 1995, now U.S. Pat. No. 5,560,933, which is a continuation-in-part of U.S. Ser. No. 08/023,698, filed Feb. 22, 1993, the contents of each of which are hereby incorporated by reference herein in their entirety.

FIELD OF THE INVENTION

The present invention relates to methods for the production of particulate vehicles for the intravenous administration of pharmacologically active agents, as well as novel compositions produced thereby. In a particular aspect, the invention relates to methods for the in vivo delivery of substantially water insoluble pharmacologically active agents (e.g., the anticancer drug paclitaxel, the active ingredient of Taxol™). In another aspect, dispersible colloidal systems containing water insoluble pharmacologically active agents are provided. The suspended particles are encased in a polymeric shell formulated from a biocompatible polymer, and have a diameter of less than about 1 micron. Invention colloidal systems can be prepared without the use of conventional surfactant or any polymeric core matrix. In a presently preferred aspect of the invention, there is provided a method for preparation of extremely small particles which can be sterile-filtered. The polymeric shell contains particles of pharmacologically active agent, and optionally a biocompatible dispersing agent in which pharmacologically active agent can be either dissolved or suspended. Thus, the invention provides a drug delivery system in either liquid form or in the form of a redispersible powder. Either form provides both immediately bioavailable drug molecules (i.e., drug molecules which are molecularly bound to a protein), and pure drug particles coated with a protein.

BACKGROUND OF THE INVENTION

Intravenous drug delivery permits rapid and direct equilibration with the blood stream which carries the medication to the rest of the body. To avoid the peak serum levels which are achieved within a short time after intravascular injection, administration of drugs carried within stable carriers would allow gradual release of the drugs inside the intravascular compartment following a bolus intravenous injection of the therapeutic nanoparticles.

Injectable controlled-release nanoparticles can provide a pre-programmed duration of action, ranging from days to weeks to months from a single injection. They also can offer several profound advantages over conventionally administered medicaments, including automatic assured patient compliance with the dose regimen, as well as drug targeting to specific tissues or organs (Tice and Gilley, *Journal of Controlled Release* 2:343–352 (1985)).

Microparticles and foreign bodies present in the blood are generally cleared from the circulation by the "blood filtering organs", namely the spleen, lungs and liver. The particulate matter contained in normal whole blood comprises red blood cells (typically 8 microns in diameter), white blood cells (typically 6–8 microns in diameter), and platelets (typically 1–3 microns in diameter). The microcirculation in most organs and tissues allows the free passage of these blood cells. When microthrombii (blood clots) of size greater than 10–15 microns are present in circulation, a risk of infarction or blockage of the capillaries results, leading to ischemia or oxygen deprivation and possible tissue death. Injection into the circulation of particles greater than 10–15 microns in diameter, therefore, must be avoided. A suspension of particles less than 7–8 microns is, however, relatively safe and has been used for the delivery of pharmacologically active agents in the form of liposomes and emulsions, nutritional agents, and contrast media for imaging applications.

The size of particles and their mode of delivery determines their biological behavior. Strand et al. (in *Microspheres-Biomedical Applications*, ed. A. Rembaum, pp 193–227, CRC Press (1988)) have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages.

Pharmaceuticals that are water-insoluble or poorly water-soluble and sensitive to acid environments in the stomach cannot be conventionally administered (e.g., by intravenous injection or oral administration). The parenteral administration of such pharmaceuticals has been achieved by emulsification of the oil solubilized drug with an aqueous liquid (such as normal saline) in the presence of surfactants or emulsion stabilizers to produce stable microemulsions. These emulsions may be injected intravenously, provided the components of the emulsion are pharmacologically inert. U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. WO85/00011 describes pharmaceutical microdroplets of an anaesthetic coated with a phospholipid such as dimyristoyl phosphatidylcholine having suitable dimensions for intradermal or intravenous injection.

An example of a water-insoluble drug is paclitaxel, a natural product first isolated from the Pacific Yew tree, *Taxus brevifolia*, by Wani et al. (*J. Am. Chem. Soc.* 93:2325 (1971)). Among the antimitotic agents, paclitaxel, which contains a diterpene carbon skeleton, exhibits a unique mode of action on microtubule proteins responsible for the formation of the mitotic spindle. In contrast with other antimitotic agents such as vinblastine or colchicine, which prevent the assembly of tubulin, paclitaxel is the only plant product known to inhibit the depolymerization process of tubulin, thus preventing the cell replication process.

Paclitaxel, a naturally occurring diterpenoid, has been shown to have significant antineoplastic and anticancer effects in drug-refractory ovarian cancer. Paclitaxel has shown excellent antitumor activity in a wide variety of tumor models such as the B16 melanoma, L1210 leukemias, MX-1 mammary tumors, and CS-1 colon tumor xenografts. Several recent press releases have termed Taxol™, a paclitaxel formulation, as the new anticancer wonder-drug. Indeed, Taxol™ has recently been approved by the Federal Drug Administration for treatment of ovarian cancer. The poor aqueous solubility of paclitaxel, however, presents a problem for human administration. Indeed, the delivery of drugs that are inherently insoluble or poorly soluble in an aqueous medium can be seriously impaired if oral delivery is not effective. Accordingly, currently used paclitaxel formulations (e.g., Taxol™) require a cremaphor to solubilize the drug. The human clinical dose range is 200–500 mg. This dose is dissolved in a 1:1 solution of ethanol:cremaphor and diluted to one liter of fluid given intravenously. The cremaphor currently used is polyethoxylated castor oil.

In phase I clinical trials, paclitaxel itself did not show excessive toxic effects, but severe allergic reactions were caused by the emulsifiers employed to solubilize the drug to form Taxol™, the conventional formulation of paclitaxel. The current regimen of administration involves treatment of the patient with antihistamines and steroids prior to injection of the drug to reduce the allergic side effects of the cremaphor.

In an effort to improve the water solubility of paclitaxel, several investigators have modified its chemical structure with functional groups that impart enhanced water-solubility. Among them are the sulfonated derivatives (Kingston et al., U.S. Pat. No. 5,059,699 (1991)), and amino acid esters (Mathew et al., J. Med. Chem. 35:145–151 (1992)) which show significant biological activity. Modifications to produce a water-soluble derivative facilitate the intravenous delivery of paclitaxel dissolved in an innocuous carrier such as normal saline. Such modifications, however, add to the cost of drug preparation, may induce undesired side-reactions and/or allergic reactions, and/or may decrease the efficiency of the drug.

Protein microspheres have been reported in the literature as carriers of pharmacological or diagnostic agents. Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored. Leucuta et al. (*International Journal of Pharmaceutics* 41 :213–217 (1988)) describe the method of preparation of heat denatured microspheres.

The procedure for preparing chemically crosslinked microspheres involves treating the emulsion with glutaraldehyde to crosslink the protein, followed by washing and storage. Lee et al. (*Science* 213:233–235 (1981)) and U.S. Pat. No. 4,671,954 teach this method of preparation.

The above techniques for the preparation of protein microspheres as carriers of pharmacologically active agents, although suitable for the delivery of water-soluble agents, are incapable of entrapping water-insoluble ones. This limitation is inherent in the technique of preparation which relies on crosslinking or heat denaturation of the protein component in the aqueous phase of a water-in-oil emulsion. Any aqueous-soluble agent dissolved in the protein-containing aqueous phase may be entrapped within the resultant crosslinked or heat-denatured protein matrix, but a poorly aqueous-soluble or oil-soluble agent cannot be incorporated into a protein matrix formed by these techniques.

One conventional method for manufacturing drug-containing nanoparticles comprises dissolving polylactic acid (or other biocompatible, water insoluble polymers) in a water-immiscible solvent (such as methylene chloride or other chlorinated, aliphatic, or aromatic solvent), dissolving the pharmaceutically active agent in the polymer solution, adding a surfactant to the oil phase or the aqueous phase, forming an oil-in-water emulsion by suitable means, and evaporating the emulsion slowly under vacuum. If the oil droplets are sufficiently small and stable during evaporation, a suspension of the polymer in water is obtained. Since the drug is initially present in the polymer solution, it is possible to obtain by this method, a composition in which the drug molecules are entrapped within particles composed of a polymeric matrix. The formation of microspheres and nanoparticles by using the solvent evaporation method has been reported by several researchers (see, for example, Tice and Gilley, in *Journal of Controlled Release* 2:343–352 (1985); Bodmeier and McGinity, in *Int. J. Pharmaceutics* 43:179 (1988); Cavalier et al., in *J. Pharm. Pharmacol.* 38:249 (1985); and D'Souza et al., WO 94/10980) while using various drugs.

Bazile et. al., in *Biomaterials* 13:1093 (1992), and Spenlehauer et al., in Fr Patent 2 660 556, have reported the formation of nanoparticles by using two biocompatible polymers, where one polymer (e.g., polylactide) is dissolved in the organic phase, together with an active component such as a drug, and the other polymer, such as albumin is used as the surface active agent. After emulsification and removal of the solvent, nanoparticles are formed, in which the drug is present inside the polymeric matrix of the polylactide particles.

The properties of the polymer solution from which the polymeric matrix is formed are very important to obtain the proper emulsion in the first stage. For example, polylactide (the polymer commonly used in the preparation of injectable nanoparticles), has a surface activity which causes the rapid adsorption thereof at the dichloromethane-water interface, causing reduced interfacial tension (see, for example, Boury et al., in *Langmuir* 11:1636 (1995)), which in turn improves the emulsification process. In addition, the same researchers found that Bovine Serum Albumin (BSA) interacts with the polylactide, and penetrates into the polylactide monolayer present at the oil-water interface. Therefore, it is expected, based on the above reference, that emulsification during the conventional solvent evaporation method is greatly favored by the presence of the surface active polymer (polylactide) in the nonaqueous organic phase. In fact, the presence of polylactide is not only a sufficient condition, but it is actually necessary for the formation of nanoparticles of suitable size.

Another process which is based on the solvent evaporation method comprises dissolving the drug in a hydrophobic solvent (e.g., toluene or cyclohexane), without any polymer dissolved in the organic solvent, adding a conventional surfactant to the mixture as an emulsifier, forming an oil-in-water emulsion, and then evaporating the solvent to obtain dry particles of the drug (see, for example, Sjostrom et al., in *J. Dispersion Science and Technology* 15:89–117 (1994)). Upon removal of the nonpolar solvent, precipitation of the drug inside the solvent droplets occurs, and submicron particles are obtained.

It has been found that the size of the particles is mainly controlled by the initial size of the emulsion droplets. In addition, it is interesting to note that the final particle size is reported to decrease with a decrease in the drug concentration in the organic phase. This finding is contrary to the results reported herein, wherein no conventional is surfactant is used for the preparation of nanoparticles. In addition, it is noted by the authors of the Sjostrom paper that the drug used, cholesteryl acetate, is surface active in toluene, and hence may be oriented at the oil-water interface; therefore the concentration of drug at the interface is higher, thus increasing the potential for precipitation.

Formation of submicron particles has also been achieved by a precipitation process, as described by Calvo et al. in *J. Pharm. Sci.* 85:530 (1996). The process is based on dissolving the drug (e.g., indomethacin) and the polymer (polycaprolactone) in methylene chloride and acetone, and then pouring the solution into an aqueous phase containing a surfactant (Poloxamer 188), to yield submicron size particles (216 nm). However, the process is performed at solvent concentrations at which no emulsion is formed.

OBJECTS OF THE INVENTION

Thus it is an object of this invention to deliver pharmacologically active agents (e.g., taxanes (e.g., paclitaxel, docetaxel, and the like), and the like) in unmodified form in a composition that does not cause allergic reactions due to the presence of added emulsifiers and solubilizing agents, as are currently employed in drug delivery.

It is a further object of the present invention to deliver pharmacologically active agents in a composition of microparticles or nanoparticles, optionally suspended in a suitable biocompatible liquid.

It is yet another object of the present invention to provide a method for the formation of submicron particles (nanoparticles) of pharmacologically active agents by a solvent evaporation technique from an oil-in-water emulsion using proteins as stabilizing agents optionally in the absence of any conventional surfactants and/or in the absence of any polymeric core material.

These and other objects of the invention will become apparent upon review of the specification and claims.

BRIEF DESCRIPTION OF THE INVENTION

In accordance with the present invention, we have discovered that substantially water insoluble pharmacologically active agents can be delivered in the form of microparticles or nanoparticles that are suitable for parenteral administration in aqueous suspension. This mode of delivery obviates the necessity for administration of substantially water insoluble pharmacologically active agents (e.g., paclitaxel) in an emulsion containing, for example, ethanol and polyethoxylated castor oil, diluted in normal saline (see, for example, Norton et al., in *Abstracts of the 2nd National Cancer Institute Workshop on Taxol & Taxus*, Sep. 23–24, 1992). A disadvantage of such known compositions is their propensity to produce allergic side effects.

Thus, in accordance with the present invention, there are provided methods for the formation of nanoparticles of pharmacologically active agents by a solvent evaporation technique from an oil-in-water emulsion prepared under conditions of high shear forces (e.g., sonication, high pressure homogenization, or the like), optionally without the use of any conventional surfactants and/or without the use of any polymeric core material to form the matrix of the nanoparticle. Instead, proteins (e.g., human serum albumin) are employed as a stabilizing agent.

The invention further provides a method for the reproducible formation of unusually small nanoparticles (less than 200 nm diameter), which can be sterile-filtered through a 0.22 micron filter. This is achieved by addition of a water soluble solvent (e.g., ethanol) to the organic phase and by carefully selecting the type of organic phase, the phase fraction and the drug concentration in the organic phase. The ability to form nanoparticles of a size that is filterable by 0.22 micron filters is of great importance and significance, since formulations which contain a significant amount of any protein (e.g., albumin), cannot be sterilized by conventional methods such as autoclaving, due to the heat coagulation of the protein.

In accordance with another embodiment of the present invention, we have developed compositions useful for in vivo delivery of substantially water insoluble pharmacologically active agents. Invention compositions comprise substantially water insoluble pharmacologically active agents (as a solid or liquid) coated by an optionally crosslinkable biocompatible polymer, and optionally contained within a polymeric shell. The polymeric shell is a crosslinked biocompatible polymer. The polymeric shell, containing substantially water insoluble pharmacologically active agents therein, can then be suspended in a biocompatible aqueous liquid for administration.

The invention further provides a drug delivery system in which part of the molecules of pharmacologically active agent are bound to the protein (e.g., human serum albumin), and are therefore immediately bioavailable upon administration to a mammal. The other portion of the pharmacologically active agent is contained within nanoparticles coated by protein. The nanoparticles containing the pharmacologically active agent are present as a substantially pure active component, without dilution by much, if any, polymeric matrix.

A large number of conventional pharmacologically active agents circulate in the blood stream bound to carrier proteins (through hydrophobic or ionic interactions) of which the most common example is serum albumin. Invention methods and compositions produced thereby provide for a pharmacologically active agent that is "pre-bound" to a protein (through hydrophobic or ionic interactions) prior to administration.

The present disclosure demonstrates both of the above-described modes of bioavailability for paclitaxel, an anti-cancer drug capable of binding to human serum albumin (see, for example, Kumar et al., in *Research Communications in Chemical Pathology and Pharmacology* 80:337 (1993)). The high concentration of albumin in invention particles, compared to Taxol™, provides a significant amount of the drug (i.e., paclitaxel) in the form of molecules bound to albumin, which is also the natural carrier of the drug in the blood stream.

In addition, advantage is taken of the capability of human serum albumin to bind paclitaxel, as well as other drugs, which enhances the capability of paclitaxel to absorb on the surface of the particles. Since albumin is present on the colloidal drug particles (formed upon removal of the organic solvent), formation of a colloidal dispersion which is stable for prolonged periods is facilitated, due to a combination of electrical repulsion and steric stabilization.

In accordance with the present invention, there are also provided submicron particles in powder form, which can easily be reconstituted in water or saline. The powder is obtained after removal of water by lyophilization. Human serum albumin serves as the structural component of invention nanoparticles, and also as a cryoprotectant and reconstitution aid. The preparation of particles filterable through a 0.22 micron filter according to the invention method as described herein, followed by drying or lyophilization, produces a sterile solid formulation useful for intravenous injection.

The invention provides, in a particular aspect, a composition of anti-cancer drugs, e.g., paclitaxel, in the form of nanoparticles in a liquid dispersion or as a solid which can be easily reconstituted for administration. Due to specific properties of certain drugs, e.g., paclitaxel, such compositions cannot be obtained by conventional solvent evaporation methods that rely on the use of surfactants. In the presence of various surfactants, very large drug crystals (e.g., size of about 5 microns to several hundred microns) are formed within a few minutes of storage, after the preparation process. The size of such crystals is typically much greater than the allowed size for intravenous injection.

While it is recognized that particles produced according to the invention can be either crystalline, amorphous, or a mixture thereof, it is generally preferred that the drug be present in the formulation in an amorphous form. This would lead to greater ease of dissolution and absorption, resulting in better bioavailability.

In accordance with another embodiment of the present invention, there are provided various methods of administering a pharmacologically active agent which must be administered in multiple doses over a cycle time which is less than the cycle time of administration of non-invention formulations of the pharmacologically active agent.

The invention further provides various methods of reducing the myelosuppressive effects and/or the neurotoxic effects of a pharmacologically active agent administered to a patient in need thereof.

In accordance with yet another embodiment of the present invention, there are provided methods of administering pharmacologically active agent(s) to a patient having a disease capable of treatment by the pharmacologically active agent(s). Invention methods comprise administering formulations according to the invention containing suitable pharmacologically active agent(s) to the patient. Diseases contemplated for treatment according to the invention include cancers, proliferative diseases, and the like. Administration of invention formulations can be accomplished in a variety of ways, e.g., intravenous or intraarterial, and/or can be without the use of steroids and/or cytokines, and/or can be in combination with a biochemotherapy agent; and/or the single dose levels of pharmacologically active agents can be greater than about 50 mg; and/or the cumulative dose levels of pharmacologically active agents can be greater than about 250 mg/m$^2$ every 3 weeks.

In accordance with a further embodiment of the present invention, there are provided methods of delivering a pharmacologically active agent to a localized area of a patient for sustained release of the pharmacologically active agent over an extended period of time (e.g., from about 1 day to about 1 year). Invention methods comprise administering to the patient a suitable pharmacologically active agent in the invention formulation, wherein the invention formulation has been dispersed within a matrix of suitable biocompatible material.

In accordance with yet another embodiment of the present invention, there are provided methods of orally administering pharmacologically active agent(s) to a patient in need thereof. Invention methods comprise orally administering an invention formulation of the pharmacologically active agent(s) in combination with intestinal cell efflux inhibitor(s).

In accordance with still another embodiment of the present invention, there are provided methods of administering a combination of suitable pharmacologically active agent(s) to a patient in need thereof. Invention methods comprise administering to the patient 25–75% of the conventionally effective dosage level of each of the suitable pharmacologically active agent(s) in the invention formulation.

DETAILED DESCRIPTION OF THE INVENTION

Figure 1:
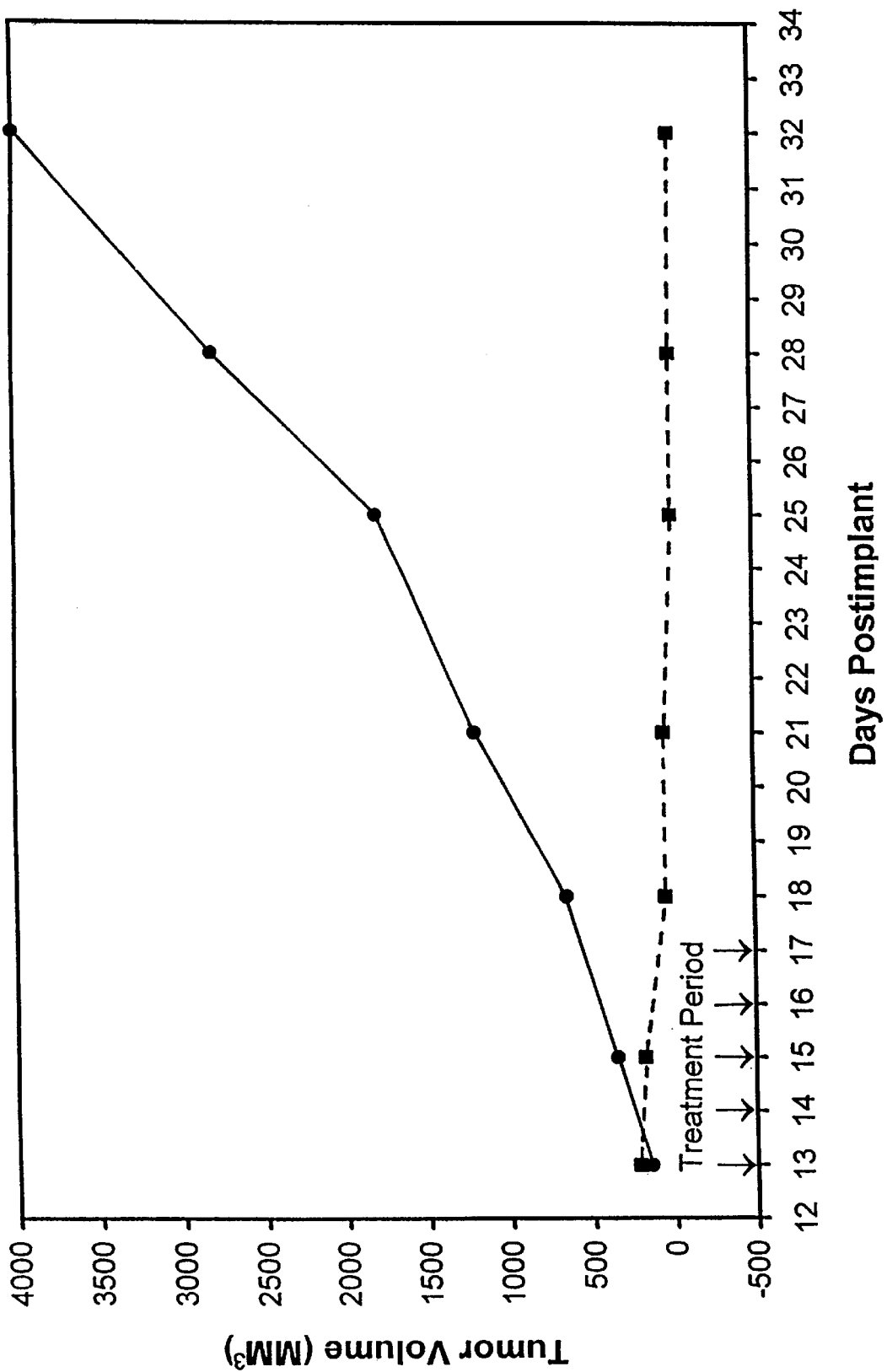
FIG. 1 presents the results of intravenous administration of paclitaxel nanoparticles to tumor bearing mice (n=5 in each group), showing a complete regression of tumor in the treatment group (n) compared with a control group receiving saline (1). Virtually uncontrolled tumor growth is seen in the control group. Dose for the treatment group is 20 mg/kg of paclitaxel administered as an intravenous bolus for five consecutive days.

In accordance with the present invention, there are provided methods for the preparation of substantially water insoluble pharmacologically active agents for in vivo delivery, said method comprising subjecting a mixture comprising:

an organic phase containing said pharmacologically active agent dispersed therein, and aqueous medium containing biocompatible polymer, wherein said mixture optionally contains substantially no surfactants, in a high pressure homogenizer to a predetermined pressure. This predetermined pressure can be in the range of about 100 up to about 100,000 psi, and preferably in the range of about 2,000 up to about 60,000 psi, and can be in a presently preferred range of about 3,000 to about 40,000 psi. In one operational embodiment, such processes can be carried out at a predetermined pressure in the range of about 3,000 psi up to about 30,000 psi. Optionally, the organic and/or aqueous phases are thereafter removed from the mixture after having been subjected to high shear conditions.

Also provided in accordance with the present invention are compositions prepared by the above-described method.

In accordance with a further embodiment of the present invention, there is provided a drug delivery system comprising particles of a solid or liquid, substantially water insoluble pharmacologically active agent, coated with a protein, wherein said protein coating has free protein associated therewith, wherein a portion of said pharmacologically active agent is contained within said protein coating and a portion of said pharmacologically active agent is associated with said free protein, and wherein the average diameter of said particles is no greater than about 1 micron.

The above-described compositions are particularly advantageous as they have been observed to provide a very low toxicity form of a variety of pharmacologically active agents, e.g., the combination of paclitaxel and albumin (as the biocompatible polymer) is a presently preferred combination because of its low toxicity. The combination of paclitaxel and albumin also has the added advantage of being substantially non-myelosuppressive.

In a preferred embodiment, the average diameter of the above-described particles is no greater than about 200 nm. Such particles are particularly advantageous as they can be subjected to sterile filtration, thereby obviating the need for more vigorous treatment to achieve sterilization of solutions containing the desired pharmacologically active agent.

As used herein, the term "in vivo delivery" refers to delivery of a pharmacologically active agent by a variety of routes of administration, as are well known to those of skill in the art. Thus, exemplary routes of administration include topical, oral, intraarticular, intracisternal, intraocular, intraventricular, intrathecal, intravenous, intramuscular, intraperitoneal, intradermal/transdermal/subcutaneous, intratracheal/inhalational, rectal (i.e., via suppository), vaginal (i.e., via pessary), intracranial, intraurethral, intrahepatic, intraarterial, intratumoral, mucosal, and the like, as well as suitable combinations of any two or more thereof. Further, administration of the pharmacologically active agent contemplated for use in the present invention can be systemic (i.e., administered to the subject as a whole via any of the above routes) or localized (i.e., administered to the specific location of the particular infirmity of the subject via any of the above routes).

Exemplary means for the systemic administration of pharmacologically active agent(s) are well known to those of skill in the art, and include oral (for example, with a sustained release formulation of the pharmacologically active agent), continuous IV infusion, infusion via bolus injection, infusion through in-dwelling catheters, and any other means which can function to deliver the pharmacologically active agent systemically to the patient in need thereof, and the like, and suitable combinations of any two or more thereof.

Exemplary means for the localized administration of pharmacologically active agent(s) include catheters, implantable or portable infusion devices, slow release delivery vehicles, and any other means which can function to deliver the pharmacologically active agent to the localized area of the infirmity to be treated, and the like, and suitable combinations of any two or more thereof.

Implantable or portable infusion devices contemplated for use in the present invention are well known to those of skill in the art, and include devices which can deliver precise and controlled amounts of the pharmacologically active agent over extended periods. Typically, these are driven by electromagnetic force, and/or osmotic force, and/or hydrostatic force, and/or gaseous pressure, and/or mechanical force. Commonly, implantable infusion devices are capable of being periodically refilled, and of being able to receive the pharmacologically active agent in solid or liquid form.

Exemplary slow release delivery vehicles include, for example, pharmacologically active agent(s) encapsulated in a colloidal dispersion system or in a polymer stabilized system. Useful colloidal dispersion systems include nanocapsules, microspheres, beads, lipid-based systems (including oil-in-water emulsions, micelles, mixed micelles, liposomes, and the like), and the like. The colloidal system presently preferred is a liposome or microsphere. Liposomes are artificial membrane vesicles which are useful as slow release delivery vehicles when injected or implanted. Some examples of lipid-polymer conjugates and liposomes are disclosed in U.S. Pat. No. , 5,631,018, which is incorporated herein by reference in its entirety. Other examples of slow release delivery vehicles are biodegradable hydrogel matrices (U.S. Pat. No. 5,041, 292), dendritic polymer conjugates (U.S. Pat. No. 5,714,166), and multivesicular liposomes (Depofoam®, Depotech, San Diego, Calif.) (U.S. Pat. Nos. 5,723,147 and 5,766.627). One type of microspheres suitable for encapsulating therapeutic agents for local injection (e.g., into subdermal tissue) is poly(D,L)lactide microspheres, as described in D. Fletcher, *Anesth. Analg.* 84:90–94, 1997.

Besides delivering an effective therapeutic dose to the site of the infirmity and decreasing the chance of systemic toxicity, localized administration also decreases the exposure of the pharmacologically active agent to degradative processes, such as proteolytic degradation and immunological intervention via antigenic and immunogenic responses, as well as to systemic clearance processes, such as sequestration in the liver.

As used herein, the term "biocompatible" describes a substance that does not appreciably alter or affect in any adverse way, the biological system into which it is introduced.

Key differences between the pharmacologically active agents coated by a stabilizing agent (and, optionally, contained in a polymeric shell of the stabilizing agent) according to the invention and protein microspheres of the prior art are in the nature of formation and the final state of the protein after formation of the particle, and its ability to carry poorly aqueous-soluble or substantially aqueous-insoluble agents. In accordance with the present invention, the stabilizing agent (e.g., a protein) can optionally be crosslinked as a result of exposure to high shear conditions in a high pressure homogenizer. High shear is used to disperse a dispersing agent containing dissolved or suspended pharmacologically active agent into an aqueous solution of a biocompatible polymer, optionally bearing sulfhydryl or disulfide groups (e.g., albumin) whereby a coating of stabilizing agent (or, optionally, a shell of crosslinked polymer) is formed around fine droplets of non-aqueous medium. The high shear conditions produce cavitation in the liquid that causes tremendous local heating and results in the formation of superoxide ions that are capable of crosslinking the polymer, for example, by oxidizing the sulfhydryl residues (and/or disrupting existing disulfide bonds) to form new, crosslinking disulfide bonds.

In contrast to the invention process, the prior art method of glutaraldehyde crosslinking is nonspecific and essentially reactive with any nucleophilic group present in the protein structure (e.g., amines and hydroxyls). Heat denaturation as taught by the prior art significantly and irreversibly alters protein structure. In contrast, disulfide formation contemplated by the present invention does not substantially denature the protein. In addition, particles of substantially water insoluble pharmacologically active agents coated with a stabilizing agent (and/or optionally contained within a shell) differ from crosslinked or heat denatured protein microspheres of the prior art because the coating (and/or polymeric shell) produced by the invention process is relatively thin compared to the diameter of the coated particle. It has been determined (by transmission electron microscopy) that the "shell thickness" of the polymeric coat is approximately 25 nanometers for a coated particle having a diameter of 1 micron (1000 nanometers). In contrast, microspheres of the prior art do not have protein shells, but rather, have protein dispersed throughout the volume of the microsphere.

As used herein, the term "micron" refers to a unit of measure of one one-thousandth of a millimeter.

Thus, in accordance with the present invention, a pharmacologically active agent is dissolved in a suitable solvent. Next, a protein (e.g., human serum albumin, other suitable polymers listed below, and the like) is added (into the aqueous phase) to act as a stabilizing agent for the formation of stable nanodroplets.

Unlike conventional methods for nanoparticle formation, polymer need not be dissolved in the mixture. Polymer can desirably be added to the mixture, however, when additional control over the nanoparticle size is warranted. When used, exemplary polymers include polylactic/polyglycolic acids and copolymers, polyvinyl alcohol, polyvinyl acetate, polyesters, and other synthetic and natural polymers functional to aid in control of the nanoparticle size, and the like, and suitable combinations of any two or more thereof.

Further, unlike conventional methods for nanoparticle formation, surfactant need not be added to the mixture. Surfactant can desirably be added to the mixture, however, when additional control over solvation of the pharmacologically active agent is warranted. When used, exemplary surfactants include sodium lauryl sulfate, lecithin, Spans, Tweens (e.g., tween 80, and the like), block copolymers (e.g., pluronics (e.g., pluronic F-68, and the like), tetronics, and the like), and other pharmaceutically acceptable surfactants, and suitable combinations of any two or more thereof.

In addition, unlike conventional methods for nanoparticle formation, foam suppressant need not be added to the mixture. Foam suppressant can desirably be added to the mixture, however, when additional control over the suppression of foam in the formation of the nanoparticles is warranted. When used, exemplary foam suppressants include silicones, oils, hydrocarbons, alcohols, other compounds which function to suppress foaming in the formation of the nanoparticles, and the like, and suitable combinations of any two or more thereof.

The order in which these components of the mixture are added to the oil phase and/or the aqueous phase can be varied depending on various conditions, as recognized by those of skill in the art.

Thus, although polymer, and/or surfactant, and/or foam suppressant can optionally be added, the oil phase employed in the preparation of invention compositions typically contains only the pharmacologically active agent dissolved in solvent, and the aqueous phase employed in the preparation of invention compositions commonly contains only the protein dissolved in aqueous medium.

Next, an emulsion is formed by homogenization under high pressure and high shear forces. Such homogenization is conveniently carried out in a high pressure homogenizer, typically operated at pressures in the range of about 100 up to about 100,000 psi, and preferably in the range of about 2,000 up to 60,000 psi, and can be in a presently preferred range of about 3,000 to about 40,000 psi. In one operational embodiment, such processes can be carried out at a predetermined pressure in the range of about 3,000 psi up to about 30,000 psi. In a presently preferred embodiment, such processes are carried out at pressures in the range of about 6,000 up to 25,000 psi, and even as high as 40,000 psi. The resulting emulsion comprises very small nanodroplets of the nonaqueous solvent (containing the dissolved pharmacologically active agent) and very small nanodroplets of the protein stabilizing agent. Acceptable methods of homogenization include processes imparting high shear and cavitation such as high pressure homogenization, high shear mixers, sonication, high shear impellers, and the like. Processes imparting shear and cavitation forces accomplish high pressure homogenization by using devices such as sonicators, homogenizers, mixers, impellers, and the like (e.g., devices commercially available from such sources as Heat Systems, Microfluidics, Avestin, Stansted, APV, Gaulin, Rannie, Ross, Silverson, Niro, and the like), and suitable combinations of any two or more thereof.

When high pressure homogenization equipment (e.g., a microfluidizer, and the like) is utilized, the product passes through an interaction chamber or a homogenizing valve which channels the product through narrow orifices with tortuous paths (10 $\mu$m–2000 $\mu$m nominal diameter) which provides high levels of shear in order to break down particle size. Different interaction chambers or homogenizing valves provide different levels of shearing force and thus break down the particle size to different extents. Interaction chambers and homogenizing valves are chosen based on their ability to reduce the particle size. The product can also be extruded under pressure through membranes or other devices having small pores whose size is in the range from about 0.025 micron to about several (e.g., up to about 200) microns.

Finally, the solvent is evaporated under reduced pressure to yield a colloidal system composed of protein coated nanoparticles of pharmacologically active agent and protein. As readily recognized by those of skill in the art, a wide variety of methods of evaporation are suitable for use in the practice of the present invention, including using device(s) selected from rotary evaporators, film evaporators, rising film evaporators, falling film evaporators, agitated film evaporators (e.g., Rototherm), concentrators, evaporator/ strippers, multistage evaporators, spray driers, lyophilizers, flash evaporators, freeze driers, or combinations of different types of evaporators such as those available from Buchi, LCI, Artisan, Pope, and Niro, or the like, or suitable combinations of any two or more thereof.

Optionally, the colloidal system produced upon evaporation of the solvent can be ultrafiltered for further concentration or to remove small molecules (e.g., organics, salts, contaminants, and the like). As readily recognized by those of skill in the art, this ultrafiltration can be accomplished by a variety of methodologies adaptable to the practice of the present invention, e.g., by using ultrafiltration device(s) such as those commercially available from Sartorius, Millipore, Pall, and the like. This ultrafiltration can be conducted prior to, in between, or after the optional filtration(s) identified in the succeeding paragraph, e.g., prior to conventional filtration, in between the stages of prefiltration and sterile filtration or after sterile filtration.

As a further optional step, the colloidal system produced upon evaporation of the solvent can be conventionally filtered and/or sterilized by filtration through sterilizing filter(s) (e.g., sterilizing filters such as membrane filters, track etched filters, depth filters and the like, and suitable combinations of any two or more thereof). Exemplary sterilizing filters are commercially available from Sartorius, Millipore, Gelman, Pall, Nuclepore, and the like. Where prefiltration is desirable, prefilter(s) can be utilized prior to sterile filtration.

In addition, the entire process of manufacture of the product (e.g., the preparation of the mixture, and/or the formation of the emulsion by homogenization, and/or the formation of the colloidal system by evaporation of the solvent, and/or the ultrafiltration, and/or the sterile filtration, as applicable) can be conducted in a batchwise mode or in a continuous mode or by a combination of batch and continuous processes.

Thus, for example, the homogenizer equipment mentioned above (for example, the microfluidizer) can be operated in a number of different ways, e.g., utilizing batch processes, continuous processes or a combination of batch and continuous processes. For example, this homogenizer equipment can be operated in the recycle mode with continuous recycling until the product meets the required particle size, and/or with discrete cycling (i.e., all of the product is processed for a fixed number of cycles (passes)), and/or in a continuous mode with recycle while removing a fixed percentage of the recycled product continuously. In addition, multiple units of the homogenizer equipment can be connected in series to achieve the desired quality for the product.

Similarly, the evaporator equipment can be operated in batch mode, continuous mode or by a combination of batch and continuous processes. For continuous mode evaporation, the product can be processed once through, or can be recycled continuously through the evaporator until such time as the desired quality of product is attained. For batch mode evaporation, the product may be processed once through the evaporator, provided the desired quality of product is achieved.

Following evaporation of solvent, the liquid suspension may be dried to obtain a powder containing the pharmacologically active agent and protein. The resulting powder can be redispersed at any convenient time into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals. Methods contemplated for obtaining this powder include freeze-drying, spray drying, and the like.

In accordance with a specific embodiment of the present invention, there is provided a method for the formation of unusually small submicron particles (nanoparticles), i.e., particles which are less than 200 nanometers in diameter. Such particles are capable of being sterile-filtered before use in the form of a liquid suspension. The ability to sterile-filter the end product of the invention formulation process (i.e., the drug particles) is of great importance since it is impossible to sterilize dispersions which contain high concentrations of protein (e.g., serum albumin) by conventional means such as autoclaving.

In order to obtain sterile-filterable particles (i.e., particles<200 nm), pharmacologically active agent(s) is initially dissolved in a substantially water immiscible organic solvent (e.g., a solvent having less than about 5% solubility in water, such as, for example, chloroform, and other suitable solvents and organic solvents as described below) at high concentration, thereby forming an oil phase containing the pharmacologically active agent(s). The oil phase employed in the process of the present invention generally contains only the pharmacologically active agent(s) dissolved in solvent.

Next, a water miscible organic solvent (e.g., a solvent having greater than about 10% solubility in water, such as, for example, ethanol) is optionally added to the oil phase at a final concentration in the range of about 1%–99% v/v, more preferably in the range of about 5%–25% v/v of the total organic phase. The water miscible organic solvent can be selected from such solvents as ethyl acetate, ethanol, tetrahydrofuran, dioxane, acetonitrile, acetone, dimethyl sulfoxide, dimethyl formamide, methyl pyrrolidinone, and the like, and other suitable solvents and organic media as described below. Alternatively, when water miscible solvent is to be added, the mixture of water immiscible solvent with the water miscible solvent is prepared first, followed by dissolution of the pharmacologically active agent(s) in the mixture.

Next, human serum albumin or any other suitable stabilizing agent as described herein is dissolved in aqueous media. This component acts as a stabilizing agent for the formation of stable nanodroplets. Optionally, a sufficient amount of the first organic solvent (i.e., the substantially water immiscible organic solvent discussed above, e.g., chloroform) is dissolved in the aqueous phase to bring it close to the saturation concentration. A separate, measured amount of the total organic phase (which now contains the pharmacologically active agent(s), the first organic solvent and optionally the second organic solvent) is added to the saturated aqueous phase, so that the phase fraction of the organic phase is between about 0.1%–50% v/v, and more preferably between 1% and 15% v/v.

As discussed above, polymer(s) and/or surfactant(s) and/or foam suppressant(s) need not be added to the mixture, although such surfactant(s) and/or foam suppressant(s) can be added when additional control over the nanoparticle size, and/or additional control over solvation of the pharmacologically active agent, and/or over the suppression of foam in the formation of the nanoparticle, respectively, is desirable.

Next, a mixture composed of micro and nanodroplets is formed by homogenization at low shear forces. This can be accomplished in a variety of ways, as can readily be identified by those of skill in the art, employing, for example, a conventional laboratory homogenizer operated in the range of about 2,000 up to about 15,000 rpm. This is followed by homogenization under high pressure (i.e., in the range of about 100 up to about 100,000 psi, and preferably in the range of about 2,000 up to about 60,000 psi, and can be in a presently preferred range of about 3,000 to about 40,000 psi). In one operational embodiment, such high pressure homogenization can be carried out at a predetermined pressure in the range of about 3,000 psi up to about 30,000 psi. The resulting mixture comprises an aqueous protein solution (e.g., human serum albumin), the water insoluble pharmacologically active agent, and the organic solvent(s). Finally, solvent is rapidly evaporated under vacuum to yield a colloidal dispersion system (pharmacologically active agent and protein) in the form of extremely small nanoparticles (i.e., particles in the range of about 10nm–200 nm diameter), and thus can be sterile-filtered, and optionally conventionally filtered and/or ultra-filtered. The preferred size range of the particles is between about 50 nm–170 nm, depending on the formulation and operational parameters.

Colloidal systems prepared in accordance with the present invention may be further converted into powder form by removal of the water therefrom, e.g., by lyophilization at a suitable temperature-time profile. As recognized by those of skill in the art, other conventional modes of water removal (e.g., spray drying) can be adapted to the practice of the present invention. The protein (e.g., human serum albumin) itself acts as a cryoprotectant, and the powder is easily reconstituted by addition of water, saline or buffer, without the need to use such conventional cryoprotectants as mannitol, sucrose, glycine, and the like. While not required, it is of course understood that conventional cryoprotectants may be added to invention formulations if so desired.

The coating on the pharmacologically active agent(s) (e.g., the polymeric shell containing solid or liquid cores of pharmacologically active agent(s)) allows for the delivery of high doses of the pharmacologically active agent in relatively small volumes. This minimizes patient discomfort at receiving large volumes of fluid and minimizes hospital stay. In addition, the walls of the polymeric shell or coating are generally completely degradable in vivo by proteolytic enzymes (e.g., when the polymer is a protein), resulting in no side effects from the delivery system as is the case with current formulations.

According to this embodiment of the present invention, particles of substantially water insoluble pharmacologically active agents have a cross-sectional diameter of no greater than about 10 microns. A cross-sectional diameter of less than 5 microns is more preferred, while a cross-sectional diameter of less than 1 micron is presently the most preferred for the intravenous route of administration.

Substantially water insoluble pharmacologically active agents contemplated for use in the practice of the present invention include pharmaceutically active agents, diagnostic agents, agents of nutritional value, and the like. Examples of pharmaceutically active agents include:

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

anesthetics (e.g., cyclopropane, enflurane, halothane, isoflurane, methoxyflurane, nitrous oxide, propofol, and the like);

antiasthmatics (e.g., Azelastine, Ketotifen, Traxanox, and the like);

antibiotics (e.g., neomycin, streptomycin, chloramphenicol, cephalosporin, ampicillin, penicillin, tetracycline, and the like);

antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

antidiabetics (e.g., biguanides, hormones, sulfonylurea derivatives, and the like);

antifungal agents (e.g., griseofulvin, keloconazole, amphotericin B, Nystatin, candicidin, and the like);

antihypertensive agents (e.g., propanolol, propafenone, oxyprenolol, Nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like);

anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like);

antineoplastics (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), vinblastine, vincristine, tamoxifen, piposulfan, and the like);

antianxiety agents (e.g., lorazepam, buspirone hydrochloride, prazeparn, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like);

immunosuppressive agents (e.g., cyclosporine, azathioprine, mizoribine, FK506 (tacrolimus), and the like);

antimigraine agents (e.g., ergotamine tartrate, propanolol hydrochloride, isometheptene mucate, dichloralphenazone, and the like);

sedatives/hypnotics (e.g., barbiturates (e.g., pentobarbital, pentobarbital sodium, secobarbital sodium, and the like), benzodiazapines (e.g., flurazepam hydrochloride, triazolam, tomazeparm, midazolam hydrochloride, and the like), and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like), and the like);

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate, and the like);

antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like);

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid, and the like);

hemorheologic agents (e.g., pentoxifylline, and the like);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

antiparkinson agents (e.g., ethosuximide, and the like);

antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate, and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

anti-infectives (e.g., GM-CSF, and the like);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate, and the like), anticholinergic agents (e.g., ipratropium bromide, and the like), xanthines (e.g., aminophylline, dyphylline, metaproterenol sulfate, aminophylline, and the like), mast cell stabilizers (e.g., cromolyn sodium, and the like), inhalant corticosteroids (e.g., flurisolidebeclomethasone dipropionate, beclomethasone dipropionate monohydrate,and the like), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate,and the like), estrogens (e.g., estradiol, estropipate, conjugated estrogens, and the like), progestins (e.g., methoxyprogesterone acetate, norethindrone acetate, and the like), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium, and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically useful protein, including any of the proteins described herein, and the like);

agents useful for erythropoiesis stimulation (e.g., erythropoietin, and the like);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

oil-soluble vitamins (e.g., vitamins A, D, E, K, and the like);

as well as other drugs such as mitotane, visadine, halonitrosoureas, anthrocyclines, ellipticine, and the like.

Additional examples of pharmaceutically active agents include those compounds which are substantially water insoluble and which are listed in the "Therapeutic Category and Biological Activity Index" of *The Merck Index* (12th Ed'n, 1996), the entire relevant contents of which are hereby incorporated by reference.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accommodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

Pharmacologically active agent(s) can be present in a broad range of concentrations in the invention composition, as determined by the end use application of the invention composition. For example, pharmacologically active agent (s) can be present in the invention composition in a range from about 0.0001% w/v to about 90% w/v, as measured in the final mixture prior to evaporation and lyophilization. In one operational embodiment, when the pharmacologically active agent is paclitaxel, the concentration of the pharmacologically active agent in the organic solvent(s) (i.e., prior to addition of any other optional components of the mixture) can be in the range from about 0.001 mg/ml to about 1000 mg/ml.

A number of biocompatible polymers may be employed in the practice of the present invention for the formation of the stabilizing agent which coats (and, optionally, for the formation of the polymeric shell which surrounds) the substantially water insoluble pharmacologically active agents. Essentially any polymer, natural or synthetic, optionally bearing sulfhydryl groups or disulfide bonds within its structure, may be utilized for the preparation of a coating (e.g., a disulfide crosslinked shell, and the like) about particles of substantially water insoluble pharmacologically active agents. The optional sulfhydryl groups or disulfide linkages may be preexisting within the polymer structure or they may be introduced by a suitable chemical modification. For example, natural polymers such as proteins, peptides, polynucleic acids, polysaccharides (e.g., starch, cellulose, dextrans, alginates, chitosan, pectin, hyaluronic acid, and the like), proteoglycans, lipoproteins, and so on, are candidates for such modification.

Proteins contemplated for use as stabilizing agents in accordance with the present invention include albumins (which contain 35 cysteine residues), immunoglobulins, caseins, insulins (which contain 6 cysteines), hemoglobins (which contain 6 cysteine residues per $a_2\beta_2$ unit), lysozymes (which contain 8 cysteine residues), immunoglobulins, a-2-macroglobulin, fibronectins, vitronectins, fibrinogens, lipases, and the like. Proteins, peptides, enzymes, antibodies and combinations thereof, are general classes of stabilizers contemplated for use in the present invention.

A presently preferred protein for use in the formation of a coating (e.g., a polymeric shell) is albumin. Optionally, proteins such as a-2-macroglobulin, a known opsonin, could be used to enhance uptake of the coated (e.g., shell encased) particles of substantially water insoluble pharmacologically active agents by macrophage-like cells, or to enhance the uptake of the coated (e.g., shell encased) particles into the liver and spleen. Specific antibodies may also be utilized to target the nanoparticles to specific locations.

Similarly, synthetic polypeptides containing cysteine residues are also good candidates for formation of a coating (e.g., a shell) about the substantially water insoluble pharmacologically active agents. These synthetic polypeptides can be chemically unmodified, or, optionally, chemically modified (for example, by the introduction of sulfhydryl and/or disulfide linkages).

Exemplary unmodified synthetic polypeptides contemplated for use in the practice of the present invention are such materials as synthetic polyamino acids (optionally containing cysteine residues and/or disulfide groups), polyvinyl alcohol, polyhydroxyethyl methacrylate, polyacrylic acid, polyethyloxazoline, polyacrylamide, polyvinyl pyrrolidinone, polyalkylene glycols, polylactides, polyglycolides, polycaprolactones, or copolymers thereof, and the like, and suitable combinations of any two or more thereof.

In addition, the unmodified synthetic polypeptides contemplated for use in the practice of the present invention listed above are good candidates for chemical modification (for example, by the introduction of sulfhydryl and/or disulfide linkages) and coating formation (e.g., shell formation, caused, for example, by the crosslinking thereof). Thus, for example, contemplated for use in the practice of the present invention are such materials as polyvinyl alcohol modified to contain free sulfhydryl groups and/or disulfide groups; polyhydroxyethyl methacrylate modified to contain free sulfhydryl groups and/or disulfide groups; polyacrylic acid modified to contain free sulfhydryl groups and/or disulfide groups; polyethyloxazoline modified to contain free sulfhydryl groups and/or disulfide groups; polyacrylamide modified to contain free sulfhydryl groups and/or disulfide groups; polyvinyl pyrrolidinone modified to contain free sulfhydryl groups and/or disulfide groups; polyalkylene glycols modified to contain free sulfhydryl groups and/or disulfide groups; polylactides, polyglycolides, polycaprolactones, or copolymers thereof, modified to contain free sulfhydryl groups and/or disulfide groups; as well as mixtures of any two or more thereof.

Suitable mixtures of any two or more of the foregoing biocompatible polymers are also contemplated for use in the practice of the present invention.

Biocompatible polymer(s) (i.e., the stabilizing agent) is typically added at a concentration in the range of about 0.001 to about 50% (w/v), more preferably in the range of about 0.1% to about 25% (w/v), with a presently preferred range of about 0.5% to about 5% (w/v), as measured in the final mixture prior to evaporation and lyophilization.

Suitable solvents utilized in accordance with the present invention include chloroform, methylene chloride, ethyl acetate, ethanol, tetrahydrofuran, dioxane, acetonitrile, acetone, dimethyl sulfoxide, dimethyl formamide, methyl pyrrolidinone, and the like, as well as mixtures of any two or more thereof. Additional solvents contemplated for use in the practice of the present invention include soybean oil, coconut oil, olive oil, safflower oil, cotton seed oil, sesame oil, orange oil, limonene oil, C1–C20 alcohols (e.g., 1-butanol, 2-butanol, 1-pentanol, 3-methyl 1-butanol, and the like), C2–C20 esters (e.g., butyl acetate, isobutyl acetate, isopropyl acetate, n-isopropyl acetate, and the like), C3–C20 ketones, polyethylene glycols, aliphatic hydrocarbons (e.g., heptane, pentane, and the like), aromatic hydrocarbons, halogenated hydrocarbons, and combinations thereof.

Additionally, in the preparation of invention compositions, a wide variety of organic media can also be employed to suspend or dissolve the substantially water insoluble pharmacologically active agent. Organic media contemplated for use in the practice of the present invention include any nonaqueous liquid that is capable of suspending or dissolving the pharmacologically active agent, but does not chemically react with either the polymer employed to produce the shell, or the pharmacologically active agent itself. Examples include vegetable oils (e.g., soybean oil, olive oil, and the like), coconut oil, safflower oil, cotton seed oil, sesame oil, orange oil, limonene oil, aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 2–30 carbon atoms (e.g., octanol, and the like), aliphatic or aromatic esters having 2–30 carbon atoms (e.g., ethyl caprylate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$, $CH_2Cl_2$, $CH_2Cl$—$CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Especially preferred combinations of organic media contemplated for use in the practice of the present invention typically have a boiling point of no greater than about 200° C., and include volatile liquids such as dichloromethane, chloroform, ethyl acetate, benzene, and the like (i.e., solvents that have a high degree of solubility for the pharmacologically active agent, and are soluble in the other organic medium employed), along with a higher molecular weight (less volatile) organic medium. When added to the other organic medium, these volatile additives help to drive the solubility of the pharmacologically active agent into the organic medium. This is desirable since this step is usually time consuming. Following dissolution, the volatile component may be removed by evaporation (optionally under vacuum).

Suitable solvent and/or organic media is typically added at a concentration in the range of about 0.01% (w/v) to about 50% (w/v), as measured in the final mixture prior to evaporation and lyophilization.

Particles of pharmacologically active agent(s) associated with a coating (e.g., a polymeric shell), prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

In accordance with a further embodiment of the present invention, there are provided methods of administering a pharmacologically active agent which must be administered in multiple doses over a cycle time which is less than the cycle time of administration of non-invention formulations of the pharmacologically active agent. Invention methods comprise administering the pharmacologically active agent in the invention formulation over a reduced cycle time.

As utilized herein, "cycle time" means the time between administration of consecutive single doses of a pharmacologically active agents which must be administered in multiple doses. Reduced cycle times contemplated for use in the present invention can be described in both absolute and percentage terms. Measured in absolute terms, reduced cycle times are cycle times which have been reduced from the cycle time of the conventional mode of administration of the same dose by any number of days from about 1 day to about 18 days. Measured in percentage terms, reduced cycle times are cycle times which have been reduced from the cycle time of the conventional mode of administration of the same dose by about 5% up to about 85% of the cycle time of the conventional mode of administration of the same dose.

Thus, when the pharmacologically active agent is a taxane (e.g., paclitaxel, docetaxel, and the like), the invention formulation of this taxane can be administered in multiple doses at a reduced cycle time of 1–20 days as required to provide maximum benefit from treatment. The reduced cycle time afforded by the low toxicity of the invention formulations permits more flexibility in treatment than the higher cycle time (i.e., not less than 3 weeks) necessitated by the higher toxicity of conventional formulations of paclitaxel (i.e., Taxol™) and docetaxel (i.e., Taxotere™).

In accordance with another embodiment of the present invention, there are provided methods of reducing the myelosuppressive effects of a pharmacologically active agent administered to a patient in need thereof. Invention methods comprise administering the pharmacologically active agent in the invention formulation. In one aspect of this embodiment of the invention, the pharmacologically active agent is a taxane (e.g., paclitaxel, docetaxel, and the like).

In accordance with an additional embodiment of the present invention, there are provided methods of reducing the neurotoxicity of a pharmacologically active agent administered to a patient in need thereof. Invention methods comprise administering the pharmacologically active agent in the invention formulation. In one aspect of this embodiment of the invention, the pharmacologically active agent is a taxane (e.g., paclitaxel, docetaxel, and the like).

In accordance with a further embodiment of the present invention, there are provided methods of administering pharmacologically active agent(s) to a patient having a disease capable of treatment by the pharmacologically active agent(s). Invention methods comprise administering suitable pharmacologically agent(s) in the invention formulation to the patient.

Accordingly, when the disease is a proliferative disease (e.g., psoriasis, multiple sclerosis, vascular restinosis, and the like), one aspect of this embodiment comprises administering suitable pharmacologically active agent(s) capable of treating the proliferative disease in the invention formulation to a patient in need thereof. Optionally, the administration is intravenous and/or the formulation is substantially free of surfactant. In one example of this aspect, suitable pharmacologically active agent(s) comprise anti-neoplastic agent(s) (for example, taxane (e.g., paclitaxel, docetaxel, and the like), and the like), or the like.

Similarly, when the disease is a cancer treatable by systemic administration of pharmacologically active agent (s), a further aspect of this embodiment comprises administering suitable pharmacologically active agent(s) capable of treating the cancer in the invention formulation to a patient having the cancer. Administration can be accomplished in a variety of ways, e.g., intravenously. In one example of this aspect, suitable pharmacologically active agent(s) comprise an anti-neoplastic agent (for example, a taxane (e.g., paclitaxel, docetaxel, and the like), and the like), or the like; and/or the cancer treatable by systemic administration is selected from metastatic breast cancers, malignant melanomas, lung cancers, ovarian cancers, head and neck cancers, prostate cancers, or the like.

In addition, when the disease is a cancer treatable by localized administration of pharmacologically active agent (s), an additional aspect of this embodiment comprises administering suitable pharmacologically active agent(s) capable of treating the cancer in the invention formulation to a patient having the cancer. Administration can be accomplished in a variety of ways, e.g., intraarterially and/or via injection. In an example of this aspect, suitable pharmacologically active agent(s) comprise an anti-neoplastic agent (for example, a taxane (e.g., paclitaxel, docetaxel, and the like), and the like), or the like; and/or the cancer treatable by localized administration is selected from primary and secondary liver tumors (e.g., hepatocellular carcinoma, multifocal hepatoma, and the like), solid tumors with local-regional involvement (e.g., metastatic breast cancer, prostatic cancer, pancreatic cancer, non-small cell lung cancer (squamous cell cancer), colon cancer, renal cancer, intestinal sarcoma, esophageal cancer, melanoma, ependymoma, head and/or neck cancer, and the like), or the like. The dose of suitable pharmacologically active agent administered in accordance with this aspect of the present invention is typically larger than doses administered as part of conventional formulations, and is commonly greater than about 50 mg.

Further, when conventional administration of the suitable pharmacologically active agent(s) requires corticosteroid premedication, an additional aspect of this embodiment comprises administering to the patient the suitable pharmacologically active agent(s) in the invention formulation without the use of any steroid(s). Administration can be accomplished in a variety of ways, e.g., intravenously. In one example of this aspect, the suitable pharmacologically active agent(s) whose conventional administration requires corticosteroid premedication comprises a taxane (e.g., paclitaxel, docetaxel, and the like), or the like; and/or the disease is selected from cancers (e.g., metastatic melanomas, renal cell carcinomas, and the like), or the like.

As a further optional step of this aspect, biochemotherapy agent(s) can be administered to the patient in combination with the suitable pharmacologically active agent(s) in the invention formulation without the use of any steroid(s). These biochemotherapy agent(s) can be administered prior to and/or concurrently with, as well as separately from or jointly with, the suitable pharmacologically active agent(s) in the invention formulation. In one example of this aspect, the biochemotherapy agents are selected from cytokines (e.g., interleukins (e.g., IL-2), interferons, G-CSF, and the like), or the like.

In addition, when conventional administration of a particular dose regimen (e.g., as described by dose level, cycle time, and the like) of the suitable pharmacologically active agent(s) requires further administration of a cytokine, an additional aspect of this embodiment comprises administering to the patient the suitable pharmacologically active agent(s) in the invention formulation without the use of any cytokine.

Particular dose regimens which require further administration of a cytokine can be readily determined by those of skill in the art. Exemplary dose regimens include administration of a suitable pharmacologically active agent (e.g., taxane (for example, paclitaxel, docetaxel, and the like), and the like) at a cumulative dose of greater than about 250 mg/m$^2$ every 3 weeks, a cumulative dose of greater than about 100–130 mg/m$^2$ every 1 week, and the like.

In one example of this aspect, the suitable pharmacologically active agent whose conventional administration at a particular dose regimen requires further administration of a cytokine comprises an anti-neoplastic agent (for example, taxane(s) (e.g., paclitaxel, docetaxel, and the like), and the like), or the like; and/or the disease is selected from cancers (e.g., metastatic melanomas, renal cell carcinomas, and the like), or the like.

In accordance with another embodiment of the present invention, there are provided methods of delivering pharmacologically active agent(s) to a localized area of a patient for sustained release of the pharmacologically active agent(s) over an extended period of time. Invention methods comprise administering to the patient a suitable pharmacologically active agent(s) in the invention formulation, wherein the invention formulation has been dispersed within a matrix of suitable biocompatible material. Administration can be accomplished in a variety of ways, e.g., intravenously. In one aspect of this embodiment of the invention, the suitable pharmacologically active agent is a taxane (e.g., paclitaxel, docetaxel, and the like); the localized areas are selected from sites of brain tumors, sites of tumors within the peritoneal cavity (e.g., ovarian cancer, metastatic disease, and the like), or the like; and the extended period of time is in a range from about 1 day to about 1 year.

Optionally, temperature sensitive materials (e.g., copolymers of polyacrylamides, copolymers of polyalkylene glycols and/or polylactide/glycolides, and the like) which gel at the local site (e.g., localized tumor site, and the like) can be utilized as the dispersing matrix for the invention formulation. In addition, gels could be made of other polysaccharides (e.g., chemically modified hyaluronic acid, and the like) and/or proteins (e.g., albumin, and the like) for controlled release of drugs from nanoparticle formulations.

These matrix-dispersed formulations can be delivered locally by a variety of means of local delivery, as discussed above (e.g., implantation directly into the brain or the peritoneal cavity after surgical removal of the brain tumor or peritoneal-located tumor, respectively, and the like). When temperature sensitive materials are utilized in the formation of this matrix, the invention formulations can be injected in a liquid formulation of the temperature sensitive materials which gels at the tumor site and provides for slow release of the pharmacologically active agent(s).

By manipulating conditions such as the concentration of sodium alginate, the concentration of the invention formulation (e.g., Capxol™, for invention formulations of paclitaxel) in the alginate solution, the crosslink density of the alginate gelled bead, and the size of the implanted beads, the rate of release of the drug can be controlled.

The invention formulations which are dispersed in matrices of the above mentioned biocompatible polymers exhibit a number of potential advantages. First, these matrix-dispersed formulations can provide a controlled, sustained release formulation of pharmacologically active agent. Second, these matrix-dispersed formulations can provide a locally deliverable formulation of pharmacologically active agent. Third, these matrix-dispersed formulations can result in lower toxicity to the local tissue surrounding the localized treatment site (e.g., the brain tissue, for administration to treat brain tumors) and lower systemic toxicity. Other advantages of these matrix-dispersed formulations are readily apparent to those of skill in the art.

In accordance with yet another embodiment of the present invention, there are provided methods of orally administering pharmacologically active agent(s) to a patient in need thereof. Invention methods comprise orally administering an invention formulation of the pharmacologically active agent(s) in combination with an intestinal cell efflux inhibitor(s).

Intestinal cell efflux inhibitor(s) contemplated for use in the present invention include cyclosporin, FK506 (i.e., tacrolimus), compounds which are effective to inhibit the function of the P-glycoprotein efflux pump (associated with intestinal cells) or other like efflux pumps, and the like, and suitable combinations of any two or more thereof.

Without limiting the scope of this embodiment of the invention, the oral administration of the formulation of the pharmacologically active agent (e.g., taxane) is believed to be facilitated by the oral administration (either in parallel (i.e., concurrent with administration of the agent formulation) or in series (i.e., prior to administration of the agent formulation)) of the intestinal cell efflux inhibitor(s) (e.g., cyclosporin and FK506). The intestinal cell efflux inhibitor(s) is believed to inhibit the function of certain efflux pumps (e.g., the P-glycoprotein efflux pump) on intestinal cell walls. Uninhibited by the intestinal cell efflux inhibitor(s), these efflux pumps would likely promptly pump any absorbed formulation of the pharmacologically active agent (e.g., taxane) out of its associated intestinal cell.

Typically, the intestinal cell efflux inhibitor(s) is contained within an invention formulation. The invention formulation of the pharmacologically active agent(s) and the invention formulation of intestinal cell efflux inhibitor(s) can be separate formulations (for serial administration), or the same formulation (for parallel administration). Once these formulation(s) have been prepared, they can be administered to a patient suffering from any disease in which treatment with the pharmacologically active agent (for example, taxanes (e.g., paclitaxel, docetaxel, and the like), and the like) shows some benefit, utilizing various dose regimens (e.g., dose amounts, cycle times, and the like) necessary to effect treatment of the disease.

In accordance with still another embodiment of the present invention, there are provided methods of administering a combination of suitable pharmacologically active agent(s) to a patient in need thereof. Invention methods comprise administering to the patient 25–75% of the conventionally effective dosage level of each of the suitable pharmacologically active agent(s) in the invention formulation. The reduced dosage levels promote lower toxicities caused by long term use of the suitable pharmacologically active agent(s), while incorporation of the suitable pharmacologically active agent(s) in the invention formulation promotes a longer half-life for the concentration of the administered agent(s) in the patient and thereby provides similar treatment effects as the conventional dosage level. In one example of this aspect, the combination of suitable pharmacologically agent(s) comprises a taxane (e.g., paclitaxel, docetaxel, and the like), and a steroid, and about 50% of the conventionally effective dosage level of each of the taxane and the steroid is administered as part of the invention formulation.

When a taxane (e.g., paclitaxel, docetaxel, and the like) is contemplated for administration in accordance with the invention methods, the amount administered per single dose typically can vary from about 1 mg/m$^2$ to about 2000 mg/m$^2$ or greater, and/or the administration time commonly can vary from about 1 minutes to about 30 minutes, and/or the cycle time between consecutive doses generally can be vary from about 1 day to about 20 days.

Those skilled in the art will recognize that several variations are possible within the scope and spirit of this invention. The organic medium within the polymeric shell may be varied, a large variety of pharmacologically active agents may be utilized, and a wide range of proteins as well as other natural and synthetic polymers may be used in the formation of the walls of the polymeric shell. Applications are also fairly wide ranging. Other than biomedical applications such as the delivery of drugs, diagnostic agents (in imaging applications), artificial blood and parenteral nutritional agents, the polymeric shell structures of the invention may be incorporated into cosmetic applications such as skin creams or hair care products, in perfumery applications, in pressure sensitive inks, and the like.

The invention will now be described in greater detail by reference to the following non-limiting examples.

EXAMPLE 1

Preparation of Nanoparticles by High Pressure Homogenization 30 mg paclitaxel is dissolved in 3.0 ml methylene chloride. The solution was added to 27.0 ml of human serum albumin solution (1% w/v). The mixture was homogenized for 5 minutes at low RPM (Vitris homogenizer, model: Tempest I. Q.) in order to form a crude emulsion, and then transferred into a high pressure homogenizer (Avestin). The emulsification was performed at 9000–18,000 psi while recycling the emulsion for at least 5 cycles. The number of cycles through the homogenizer can vary from about one up to hundreds of cycles, depending on the size of the dispersion desired. The resulting system was transferred into a Rotary evaporator, and methylene chloride was rapidly removed at 40° C., at reduced pressure (30 mm Hg), for 20–30 minutes. The resulting dispersion was translucent, and the typical diameter of the resulting paclitaxel particles was 160–220 (Z-average, Malvern Zetasizer).

The dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 2

Preparation of Nanoparticles by Sonication

The purpose of this example is to demonstrate the formation of nanoparticles of paclitaxel by using cavitation and high shear forces during a sonication process. Thus, 20 mg paclitaxel is dissolved in 1.0 ml methylene chloride. The solution is added to 4.0 ml of human serum albumin solution (5% w/v). The mixture is homogenized for 5 minutes at low RPM (Vitris homogenizer, model: Tempest I. Q.) in order to form a crude emulsion, and then transferred into a 40 kHz sonicator cell. The sonicator is performed at 60–90% power at 0 degree for 1 min (550 Sonic Dismembrator). The mixture is transferred into a Rotary evaporator, and methylene chloride is rapidly removed at 40° C., at reduced pressure (30 mm Hg), for 20–30 minutes. The typical diameter of the resulting paclitaxel particles was 350–420 nm (Z-average, Malvern Zetasizer).

The dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 3

Use of Conventional Surfactants and Proteins Results in Formation of Large Crystals The following example demonstrates the effect of adding surfactants which are used in the conventional solvent evaporation method. A series of experiments was conducted employing a similar procedure to that described in Example 1, but a surfactant such as Tween 80 (1% to 10%) is added to the organic solvent. It was found that after removal of the methylene chloride, a large number of paclitaxel crystals is obtained having an average size of 1–2 micron, as viewed by light microscopy and under polarized light. The crystals grow within a few hours to form very large needle-like crystals, with a size in the range of about 5–15 micron. A similar phenomenon is observed with other commonly used surfactants, such as Pluronic F-68, Pluronic F 127, Cremophor EL and Brij 58.

From these results it can be concluded that the conventional solvent evaporation method utilizing conventional surfactants in combination with a protein such as albumin is not suitable for the formation of submicron drug particles (e.g., paclitaxel) without a polymeric core, while using a polar solvent (e.g., methylene chloride).

EXAMPLE 4

Use of Conventional Surfactants Alone Results in Formation of Large crystals

This example demonstrates that it is not possible to form nanoparticles while using conventional surfactants, without a polymeric core material, with pharmacologically active agents which are soluble in polar, water immiscible solvents (e.g., chloroform).

30 mg paclitaxel is dissolved in 0.55 ml chloroform and 0.05 ml ethanol. The solution is added to 29.4 ml of Tween 80 solution (1% w/v), which is presaturated with 1% chloroform. The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 6 cycles. The number of cycles through the homogenizer can vary from about one up to hundreds of cycles, depending on the size of the dispersion desired. The resulting system was transferred into a Rotary evaporator, and the chloroform was rapidly removed at 40° C., at reduced pressure (30 mm Hg), for 15–30 minutes. The resulting dispersion was opaque, and contained large needle-like crystals of the drug. The initial size of the crystals (observed also by polarized light), was 0.7–5 micron. Storage of the dispersion for several hours at room temperature led to further increase in crystal size, and ultimately to precipitation.

EXAMPLE 5

Preparation of Less than 200 nm Sterile-filterable Nanoparticles

This example describes the process by which sterile-filterable drug particles can be obtained. Thus, 30 mg paclitaxel is dissolved in 0.55 ml chloroform and 0.05 ml ethanol. The solution is added to 29.4 ml of human serum albumin solution (1% w/v), which is presaturated with 1% chloroform. The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 6 cycles. The number of cycles through the homogenizer can vary from about one up to hundreds of cycles, depending on the size of the dispersion desired. The resulting system is transferred into a Rotary evaporator, and the chloroform is rapidly removed at 40° C., at reduced pressure (30 mm Hg), for 15–30 minutes. The resulting dispersion is translucent, and the typical diameter of the resulting paclitaxel particles is 140–160 nm (Z-average, Malvern Zeta Sizer). The dispersion is filtered through a 0.22 micron filter (Millipore), without any significant change in turbidity, or particle size. HPLC analysis of the paclitaxel content revealed that more than 97% of the paclitaxel was recovered after filtration, thus providing a sterile paclitaxel dispersion.

The sterile dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 6

Preparation of Less than 200 nm Sterile-filterable Nanoparticles

This example describes the process by which sterile-filterable drug particles can be obtained. Thus, 225 mg paclitaxel is dissolved in 2.7 ml chloroform and 0.3 ml ethanol. The solution is added to 97 ml of human serum albumin solution (3% w/v). The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 6 cycles. The number of cycles through the homogenizer can vary from about one up to hundreds of cycles, depending on the size of the dispersion desired. The resulting system is transferred into a Rotary evaporator, and the chloroform is rapidly removed at 40° C., at reduced pressure (30 mm Hg), for 15–30 minutes. The resulting dispersion is translucent, and the typical diameter of the resulting paclitaxel particles is 140–160 nm (Z-average, Malvern Zeta Sizer). The dispersion is filtered through a 0.22 micron filter (Sartorius, sartobran 300), without any significant change in turbidity, or particle size. HPLC analysis of the paclitaxel content typically revealed that 70–100% of the paclitaxel could be recovered after filtration, depending on the conditions employed. Thus, a sterile paclitaxel dispersion was obtained.

The sterile dispersion was aseptically filled into sterile glass vials and lyophilized without adding any cryoprotectant. The resulting cake could be easily reconstituted to the original dispersion by addition of sterile water or saline. The particle size after reconstitution was the same as before lyophilization.

EXAMPLE 7

Preparation of Less than 200 nm Sterile-filterable Nanoparticles—higher PSI

This example describes the process by which sterile-filterable drug particles can be obtained at higher homogenization pressures than utilized in Example 6.Thus, 225 mg paclitaxel is dissolved in 2.7 ml chloroform and 0.3 ml ethanol. The solution is added to 97 ml of human serum albumin solution (3% w/v). The mixture is homogenized for 5 minutes at low RPM (Vitris homogenizer, model: Tempest I. Q.) in order to form a crude emulsion, and then transferred into a high pressure homogenizer (Microfluidics). The emulsification is performed at 30,000 psi while recycling the emulsion for at least 6 cycles. The number of cycles through the homogenizer can vary from about one up to hundreds of cycles, depending on the size of the dispersion desired. The resulting system is transferred into a Rotary evaporator, and the chloroform is rapidly removed at 40° C., at reduced pressure (30 mm Hg), for 15–30 minutes. The resulting dispersion is translucent, and the typical diameter of the resulting paclitaxel particles is 120–160 nm (Z-average, Malvern Zeta Sizer). The dispersion is filtered through a 0.22 micron filter (Sartorius, sartobran 300), without any significant change in turbidity, or particle size. HPLC analysis of the paclitaxel content typically revealed that 70–100% of the paclitaxel could be recovered after filtration, depending on the conditions employed. Thus, a sterile paclitaxel dispersion was obtained.

The sterile dispersion was aseptically filled into sterile glass vials and lyophilized without adding any cryoprotectant. The resulting cake could be easily reconstituted to the original dispersion by addition of sterile water or saline. The particle size after reconstitution was the same as before lyophilization.

EXAMPLE 8

Effect of Phase Fraction of Organic Solvent on Particle Size

The following example demonstrates the importance of having an unusually low phase fraction of the organic solvent in the system.

Thus, a series of experiments was conducted following a similar procedure to that described for Example 5, except the phase fraction of the organic solvent was altered, and the ethanol content maintained at 10% v/v in the organic phase. It was found that increasing the phase fraction led to a significant increase in particle size: at 4% v/v phase fraction (above the saturation concentration, or 5% v/v total chloroform concentration) the resulting particles have a diameter of 250 nm; at 3% v/v phase fraction, the particles have a 200 nm diameter, and at 2% v/v phase fraction, the particles have a 150 nm diameter.

Clearly, only the particles prepared at very low phase fraction could be sterile-filtered.

EXAMPLE 9

Effect of Drug Concentration on Particle Size

The role of drug concentration in the organic phase is demonstrated in the following example. Two experiments were performed in which the paclitaxel concentration in the organic phase was 50 mg/ml or 75 mg/ml, while all other parameters were the same as described in Example 3. It was found that the low drug concentration yielded particles having a diameter of about 150 nm, while those prepared at the higher drug loading were smaller, i.e., 130–138 nm. When a similar experiment was performed, but with an ethanol concentration in the organic phase of about 50%, a similar trend was observed, i.e., particles were 210 nm and 156 nm in diameter, for 25 mg/ml and 50 mg/ml drug concentration, respectively.

These findings directly contradict those reported by Sjostrom et al., supra, for the formation of nanoparticles in presence of surfactants.

EXAMPLE 10

Nanoparticle Formation of a Model Drug 30 mg isoreserpine (a model drug) is dissolved in 3.0 ml methylene chloride. The solution is added to 27.0 ml of human serum albumin solution (1% w/v). The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 5 cycles. The number of cycles through the homogenizer can vary from about one up to hundreds of cycles, depending on the size of the dispersion desired. The resulting system is transferred into a Rotary evaporator, and methylene chloride is rapidly removed at 40° C., at reduced pressure (30 mm Hg), for 20–30 minutes. The resulting dispersion is translucent, and the typical diameter of the resulting isoreserpine particles was 120–140 nm (Z-average, Malvern Zetasizer). The dispersion was filtered through a 0.22 micron filter (Millipore).

The sterile dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 11

Extremely Small Particle Formation with a Model Drug

The effect of ethanol addition on reducing particle size is demonstrated for Isoreserpine. Thus, 30 mg Isoreserpine is dissolved in 2.7 ml methylene chloride and 0.3 ml ethanol. The solution is added to 27.0 ml of human serum albumin solution (1% w/v). The mixture is homogenized for 5 minutes at low RPM (Vitris homogenizer, model: Tempest I. Q.) in order to form a crude emulsion, and then transferred into a high pressure homogenizer (Avestin). The emulsification was performed at 9000–18,000 psi while recycling the emulsion for at least 5 cycles. The number of cycles through the homogenizer can vary from about one up to hundreds of cycles, depending on the size of the dispersion desired. The resulting system was transferred into a Rotary evaporator, and methylene chloride was rapidly removed at 40° C., at reduced pressure (30 mm Hg), for 20–30 minutes. The resulting dispersion was translucent, and the typical diameter of the resulting isoreserpine particles was 90–110 nm (Z-average, Malvern Zetasizer). The dispersion was filtered through a 0.22 micron filter (Millipore).

The sterile dispersion was further lyophilized for 48 hrs. without adding any cryoprotectant. The resulting cake could be easily reconstituted to the original dispersion by addition of sterile water or saline. The particle size after reconstitution was the same as before lyophilization.

EXAMPLE 12

Use of a Water Miscible Solvent Alone, Supersaturated with Drug—not Suitable for Invention Process 30 mg paclitaxel is dispersed in 0.6 ml ethanol. At this concentration (50 mg/ml), the paclitaxel is not completely soluble and forms a supersaturated dispersion. The dispersion is added to 29.4 ml of human serum albumin solution (1% w/v). The mixture is homogenized for 5 minutes at low RPM (Vitris homogenizer, model: Tempest I. Q.) in order to form a crude dispersion, and then transferred into a high pressure homogenizer (Avestin). The emulsification is performed at 9000–18,000 psi while recycling the emulsion for at least 6 cycles. The number of cycles through the homogenizer can vary from about one up to hundreds of cycles, depending on the size of the dispersion desired. The resulting system is transferred into a Rotary evaporator, and the ethanol is rapidly removed at 40° C., at reduced pressure (30 mm Hg), for 15–30 minutes. The resulting dispersion particle size is extremely broad, ranging from about 250 nm to several microns.

Observation under the microscope revealed the presence of large particles and typical needle shaped crystals of paclitaxel. These particles were too large for intravenous injection. This experiment demonstrates that the use of solvents such as ethanol that are freely miscible in water in the invention process results in the formation of large particles with very broad particle size distribution and as such cannot be used alone for the invention process. Thus, it is seen that the use of water miscible solvents is not preferred when used alone for the dissolution or dispersion of the drug component. The invention process requires that such solvents, when used, will preferably be mixed with essentially water immiscible solvents to allow efficient production of the invention nanoparticles.

EXAMPLE 13

Use of a Water Miscible Solvent Alone Containing Dissolved Drug—not Suitable for Invention Process 30 mg paclitaxel is dispersed in 1.3 ml ethanol. At this concentration (approx. 24.5 mg/ml), the paclitaxel is completely soluble in ethanol. The solution is added to 28.7 ml of human serum albumin solution (1% w/v). The mixture is homogenized for 5 minutes at low RPM (Vitris homogenizer, model: Tempest I. Q.) in order to form a crude dispersion, and then transferred into a high pressure homogenizer (Avestin). The emulsification is performed at 9000–18,000 psi while recycling the emulsion for at least 6 cycles. The number of cycles through the homogenizer can vary from about one up to hundreds of cycles, depending on the size of the dispersion desired. The resulting system is transferred into a Rotary evaporator, and the ethanol is rapidly removed at 40° C., at reduced pressure (30 mm Hg), for 15–30 minutes. The resulting dispersion particle size was extremely broad, ranging from about 250 nm to several microns. Observation under the microscope revealed the presence of large particles and typical needle shaped crystals of paclitaxel. These particles were too large for intravenous injection.

This example, in addition to Example 12 above, demonstrates that the use in the invention process of solvents such as ethanol that are freely miscible in water results in the formation of large particles with very broad particle size distribution and as such cannot be used alone for the invention process. Thus the invention process specifically excludes the use of water miscible solvents when used alone for the dissolution or dispersion of the drug component. The invention process requires that such solvents, when used, be mixed with essentially water immiscible solvents to enable formation of invention nanoparticles.

EXAMPLE 14

Determination of Physical State of Paclitaxel in Nanoparticle Form by X-ray Powder Diffraction Paclitaxel raw material is usually present as needle shaped crystals of varying sizes typically between 5–500 microns. The presence of crystals in a drug formulation for intravenous injection is obviously detrimental if crystals are present in size above a few microns due to potential blockage of capillaries. In addition, the solubility of drug crystals in general would be lower than for amorphous drug, thereby lowering the bioavailability of the drug following intravenous administration. It is also known that as the loading of the drug in a formulation is increased, the tendency for crystallization also increases. Thus it is advantageous that the formulation contain the drug in essentially amorphous form.

X-ray powder diffraction was used to determine the crystalline or non-crystalline nature of paclitaxel in the lyophilized powder formulation. The following samples were analyzed: Sample 1—Paclitaxel powder; Sample 2—Lyophilized serum albumin; Sample 3—a physical mixture of paclitaxel and albumin; and Sample 4—formulated paclitaxel. Each sample was x-rayed from 2° to 70° 2Q angles using CuKa radiation, an accelerating voltage of 40 KeV/30 mA, a step size of 0.05° 2Q and a data acquisition time of 2.0 seconds per step. Sample 1 showed strong peaks typical of a crystalline sample. The most intense paclitaxel peak was located at 5.1° 2Q. Sample 2 showed broad humps typical of amorphous material. Sample 3 showed largely the broad humps of Sample 2, but in addition, the peak at 5.1° 2Q of paclitaxel was visible. Sample 4, the formulated paclitaxel showed no evidence of crystallinity characteristic of paclitaxel and appeared identical to Sample 2, indicating the presence of substantially amorphous pharmacologically active agent in the formulated sample.

The amorphous nature of the nanoparticles produced according to the invention stands in direct contrast to the products produced by other methods described in the art for producing nanoparticles. For example, the use of grinding techniques, as described in U.S. Pat. No. 5,145,684 (Liversidge et al.), and as described by Liversidge-Merisko et al., *Pharmaceutical Research* 13(2):272–278 (1996), produces a substantially crystalline product.

EXAMPLE 15

Treatment of Tumors in an Animal Model with Paclitaxel Nanoparticles

Nanoparticles of paclitaxel (the active ingredient of Taxol™) were prepared as described above in Example 1.This formulation of the drug was tested in a MX-1 human mammary tumor xenograft model in mice. The mice were implanted subcutaneously with the MX-1 mammary tumor and the treatment was initiated when the tumor reached approximately 150–300 mg in size. This occurred by day 12 and the treatment was initiated on day 13 after initial seeding.

Tumor bearing mice were treated with paclitaxel nanoparticles at a dose of 20 mg/kg, given by bolus intravenous injection as a suspension in saline for five consecutive days. The treated group included five animals. The control tumor bearing group of five animals received only saline on the same schedule. The size of the tumors was monitored as a function of time. The control group showed a tremendous increase in tumor weight. All the animals in this group were sacrificed between day 28 and day 39.The treatment group on the other hand showed remarkable efficacy as all animals had no measurable tumors by day 25.The animals in this group were all sacrificed on day 39, at which time they showed no evidence of recurrence and no evidence of tumor. The results are shown in FIG. 1.

EXAMPLE 16

Treatment of Rheumatoid Arthritis in an Animal Model with Paclitaxel Nanoparticles Collagen induced arthritis model in the Louvain rat was used to test the therapeutic effect of paclitaxel nanoparticles on arthritis. The paw sizes of the experimental animals were monitored to evaluate the seriousness of arthritis.

Figure 2:
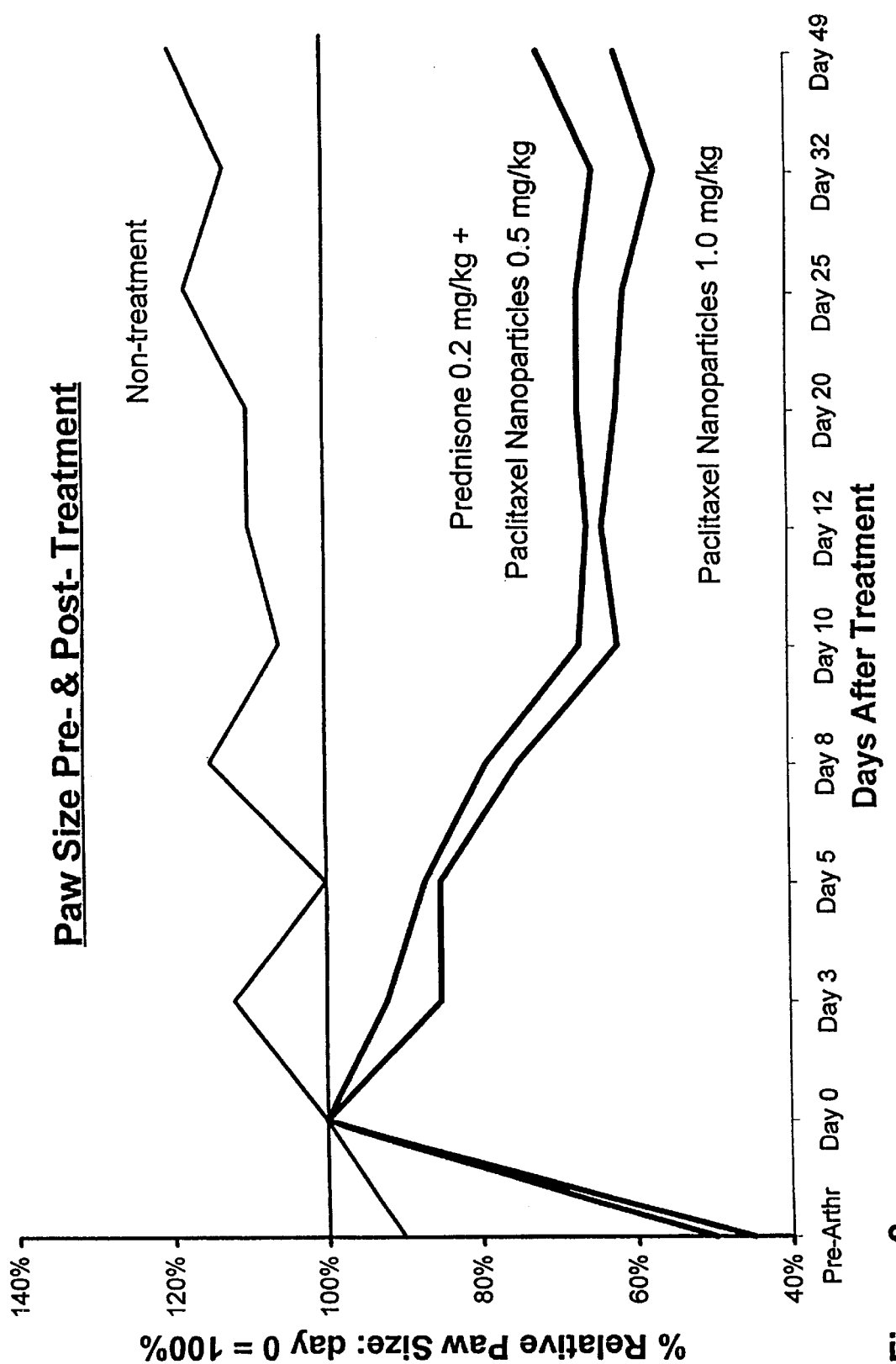
FIG. 2 presents the results of intraperitoneal administration of paclitaxel nanoparticles in rats that have developed arthritis in their paws following intradermal injection of collagen. Paw volumes are measured and indicate the severity of the disease. The paw volumes are normalized to 100% at the beginning of treatment. Day 0 represents the initiation of treatment. There are 3 groups—control group receiving saline (n=2, shown as a thin line and labelled in the figure a "non-treatment"); a first treatment group receiving paclitaxel nanoparticles at a dose of 1 mg/kg (n=4, shown as a heavy line and labelled in the figure as "paclitaxel nanoparticles 1.0 mg/kg"), and a second treatment group receiving combination therapy of paclitaxel nanoparticles at a dose of 0.5 mg/kg and prednisone at a dose of 0.2 mg/kg (n=4, shown as a heavy line and labelled in the figure as "prednisone 0.2 mg/kg+paclitaxel nanoparticles 0.5 mg/kg"). The two treatment groups show a dramatic reduction in paw volume with time, indicating a regression of arthritis, while the control group showed an increase in paw volume over the same period.

After the arthritis was fully developed (usually ~9–10 days after collagen injection), the experimental animals were divided into different groups to receive either paclitaxel nanoparticles 1 mg/kg q.o.d, or paclitaxel nanoparticles 0.5 mg/kg+prednisone 0.2 mg/kg q.o.d. (combination treatment) intraperitoneally for 6 doses, then one dose per week for three weeks. The paw sizes were measured at the beginning of treatment (day 0) and every time the drug was injected. One group received only normal saline as control. By the end of the experiment, the group receiving paclitaxel nanoparticles achieved a 42% reduction of paw size, the combination treatment group showed a 33% reduction of the paw size while the control group had about 20% increase of the paw size. Original paw size before arthritis was induced was 50%. The results are shown in FIG. 2.

In conclusion, the paclitaxel-containing nanoparticles demonstrated therapeutic effect on arthritis. To avoid side effects of long term use of both paclitaxel and the steroid, it is probably better to choose a combination treatment to get similar effect but only half the dosage of each drug.

EXAMPLE 17

In vivo Targeting of Nanoparticles

By incorporation of certain targeting moieties such as proteins, antibodies, enzymes, peptides, oligonucleotides, sugars, polysaccharides, and the like, into the protein coating of the nanoparticles, it is possible to target specific sites in the body. This targeting ability can be utilized for therapeutic or diagnostic purposes.

EXAMPLE 18

Intravenous Delivery Systems Formulated from a Variety of Materials

The materials used for the preparation of intravenous delivery systems may be polymeric (e.g., polyethylene, polyvinyl, polypropylene tubing, and the like), or glass. Standard medical grade tubing is known to contain hydrophobic moieties on the inner surfaces thereof. These moieties are thus available to come in contact with the injection solution. Indeed, such tubing is specifically tailored, as are the catheters, to present hydrophobic moieties in contact with the treatment solution so as to reduce the absorption of aqueous material to the tubing. However, any hydrophobic moieties in the treatment solution will likely bind to both the catheter tubing and other components of the delivery system. As a result, a substantial portion of a hydrophobic pharmacologically active agent can become sequestered in the inner walls of the tubing catheter and delivery vessel. Consequently, the dosing of hydrophobic pharmacologically active agents can be erratic, since a substantial portion of the active agent can become absorbed to the walls of the tubing. In critical therapeutic treatments, where the hydrophobic pharmacologically active agent is used to treat a disease, a significant reduction in the effective dose of active agent can lead to a therapeutic failure. The failure is particularly striking when employing therapeutic moieties which require that the active agent be present above a certain level, yet the therapeutic window is narrow.

A novel method for the intravenous introduction of a hydrophobic pharmacologically active agent has now been developed. By protecting the hydrophobic moieties of the active agent, through association with the hydrophobic moieties of a biocompatible coating (e.g., albumin), the propensity of the active agent to become attached to the tubing is dramatically reduced. Thus, the present invention enables the use of highly hydrophobic drugs, in combination with standard medical grade polymers and hydrophobic glasses, in which the drug is protected and therefore not absorbed onto the surface. The invention method comprises placing a protective coating of a biocompatible polymer (e.g., albumin) around the hydrophobic drug and placing the resulting composition in a hydrophobic polymeric delivery system The invention methods are therefore capable of improving the delivery of a variety of hydrophobic therapeutics.

EXAMPLE 19

Intravenous Administration of Therapeutics

Intravenous administration of therapeutics, for example, drugs, imaging agents, and the like, predisposes the therapeutic to at least one pass through the liver. As that therapeutic is filtered through the liver, a significant portion of that therapeutic is taken up and sequestered by the liver, and therefore, not available for systemic distribution. Moreover, once taken up by the liver, it is likely to be metabolized, and the resulting metabolic byproducts often have general systemic toxicities. By encapsulating the drug or other therapeutic agent in a coating according to the invention (e.g., using a protein such as albumin), liver sequestration upon intravenous administration is alleviated. Albumin, for example, is known to pass through the liver and become generally distributed throughout the patient. Thus, the sequestration of albumin by the liver does not occur to the same degree as toxic compounds or drugs which have hepatic receptors (or other mechanisms) which initiate processes which result in their removal from the blood stream. By protecting the therapeutic with a coating of a biocompatible polymer (e.g., a human albumin coating), the drug then bypasses the liver and is generally distributed through all organ systems. In accordance with one aspect of the present invention, there is provided a novel method for bypassing the liver, which comprises encapsulating a drug in a human liver albumin (essentially a physiological component). In this way, more of the drug becomes available for systemic therapy. In addition to the increased availability of the drug, there is a decrease in the production of metabolic byproducts of hepatocellular drug degradation. Both the increase in liver bypass and decrease in byproducts of drug metabolism provide a synergistic improvement in the overall drug efficacy. This improved efficacy extends to all drugs and materials that are encapsulated in human albumin.

EXAMPLE 20

Reducing Myelosuppressive Effects and General Toxicity of Drugs

Several chemotherapeutic drugs have dose limiting toxicity due to their myelosuppressive effects. Paclitaxel (the active ingredient of Taxol™) is a classic example of such a drug. When administered in its currently approved formulation of cremaphor/ethanol (i.e., Taxol™), paclitaxel produces myelosuppressive effects that limit the repeat administration of the drug and preclude retreatment of a patient for at least 3 weeks in order to allow blood counts of the patient to return to normal. It was postulated that due to the non-toxic compatible nature of the drug carrier of the present invention, viz. human albumin, the toxic side effect of myelosuppression may be greatly reduced.

Sprague dawley rats were given paclitaxel in commercial formulation (available from Bristol Myers Squibb (BMS) in cremaphor/ethanol) or prepared by the invention method as nanoparticles with albumin. Both formulations were administered by tail vein injection. A single dose level of 5 mg/kg was administered for the BMS formulation, whereas two dose levels of 5 mg/kg and 12 mg/kg were administered for the invention formulation (Capxol). The white blood cell counts of the rats were monitored daily after administration as an index of myelosuppression.

For the BMS formulation (5 mg/kg) it was found that the WBC counts dropped by 47.6% and 63.5% on day 1 and day 2 after administration, respectively, whereas for the Capxol formulation at 5 mg/kg, the WBC counts increased by 14.7% and 2.4% on day 1 and day 2, respectively. For the higher dose Capxol at 12 mg/kg, the WBC counts increased by 6.5% and 3.6% on day 1 and day 2, respectively.

These results indicate that short term myelosuppression is greatly reduced by administering the drug in the present invention formulation.

Another indicator of general toxicity is the body weight of the animal. Body weights of the rats were also monitored following administration of paclitaxel. At a dose of 5 mg/kg, the BMS formulation resulted in a reduction of body weight by 10.4% in 3 days following administration, whereas the same dose of paclitaxel administered in the invention formulation (Capxol) resulted in only a 3.9% drop in body weight, indicating the greatly reduced toxicity of the invention formulation.

EXAMPLE 21

Administration of Bolus Dose of Nanoparticle Formulation

The anticancer drug, paclitaxel, in its commercial BMS formulation with Cremaphor/ethanol, cannot be administered as an intravenous bolus. This is due to the extensive toxicity of the vehicle which results in severe anaphylactic reactions and requires patients receiving the drug to be pre-medicated with steroids, antihistamines, and the like. The BMS formulation is administered as an intravenous infusion lasting anywhere from 1 hour to 24 hours. In contrast, formulations according to the present invention, due to the use of a non-toxic carrier, can be administered to a patient readily as an intravenous bolus (i.e., in a period less than 1 hour) without the toxicity problems seen in the BMS formulation that is used clinically today.

The effective dose of paclitaxel for a patient typically lies between 200–500 mg, depending on the patient body weight or body surface. The BMS formulation has to be administered at a final dosing concentration of 0.6 mg/ml, requiring large infusion volumes (typically in the range of about 300–1000 ml). In contrast, invention formulations (e.g., Capxol) do not have these limitations and can be administered at a desired concentration. This enables clinicians to treat patients by a rapid intravenous bolus that can be administered in as little as a few minutes. For example, if the invention formulation is reconstituted to a dosing concentration of 20 mg/ml, the infusion volume for a total dose of 200–500 mg is only 10–25 ml, respectively. This is a great advantage in clinical practice.

EXAMPLE 22

Reduction in Toxicity of Paclitaxel in the Nanoparticle Formulation Compared to the Commercial Cremaphor/ethanol Formulation It is well known that the anticancer drug, paclitaxel, in its commercial BMS formulation with Cremaphor/ethanol, has extensive toxicity which results in severe anaphylactic reactions and requires patients receiving the drug to be pre-medicated with steroids, antihistamines, and the like. The toxicity of the BMS formulation was compared to the nanoparticle formulation of the present invention.

Thus, the formulations were injected intravenously through the tail vein of C57BL mice at different dose levels and toxic effects were monitored by general observation of mice after the injection.

For the BMS formulation, a dose of 30 mg/kg was uniformly lethal within 5 minutes of intravenous administration. For the same dose, the nanoparticle formulation according to the invention showed no apparent toxic effects. The nanoparticle formulation at a dose of 103 mg/kg showed some reduction in body weight of the mice, but even this high dose was not lethal. Doses of approximately 1000 mg/kg, 800 mg/kg and 550 mg/kg were all lethal but differing in time to lethality, which ranged between a few hours to 24 hours. The lethal dose of the invention formulation is greater than 103 mg/kg but less than 550 mg/kg.

Thus, the lethal dose of the invention formulation of paclitaxel is substantially higher than that of the commercial BMS formulation. This has great significance in clinical practice where higher doses of chemotherapeutic drugs may be administered for more effective oncolytic activity with greatly reduced toxicity.

EXAMPLE 23

Preparation of Nanoparticles of Cyclosporin (Capsorine I.V.) by High Pressure Homogenization 30 mg cyclosporine is dissolved in 3.0 ml methylene chloride. The solution is then added into 27.0 ml of human serum albumin solution (1% w/v). The mixture is homogenized for 5 minutes at low RPM (Vitris homogenizer model: Tempest I. Q.) in order to form a crude emulsion, and then transferred into a high pressure homogenizer (Avestin). The emulsification was performed at 9000–18,000 psi while recycling the emulsion for at least 5 cycles. The number of cycles through the homogenizer can vary from about one up to hundreds of cycles, depending on the size of the dispersion desired. The resulting system was transferred into a Rotavap and methylene chloride was rapidly removed at 40° C., at reduced pressure (30 mm Hg), for 20–30 minutes. The resulting dispersion was translucent and the typical diameter of the resulting cyclosporine particles was 160–220 (Z-average, Malvern Zetasizer).

The dispersion was further lyophilized for 48 hours, without adding any cryoprotectant. The resulting cake could be easily reconstituted to the original dispersion by addition of sterile water or saline. The particle size after reconstitution was the same as before lyophilization.

EXAMPLE 24

Preparation of Nanodroplets of Cyclosporine (Capsorine Oral) by High Pressure Homogenization 30 mg cyclosporine is dissolved in 3.0 ml of a suitable oil (sesame oil containing 10% orange oil). The solution is then added into 27.0 ml of human serum albumin solution (1% v/w). The mixture is homogenized for 5 minutes at low RPM (Vitris homogenizer, model: Tempest I. Q.) in order to form a crude emulsion, and then transferred into a high pressure homogenizer (Avestin). The emulsification is performed at 9000–18,000 psi while recycling the emulsion for at least 5 cycles. The number of cycles through the homogenizer can vary from about one up to hundreds of cycles, depending on the size of the dispersion desired. The resulting dispersion had a typical diameter of 160–220 (Z-average, Malvern Zetasizer).

The dispersion could be used directly or lyophilized for 48 hours by optionally adding a suitable cryoprotectant. The resulting cake could be easily reconstituted to the original dispersion by addition of sterile water or saline.

EXAMPLE 25

Pharmacokinetic (PK) Data for Cyclosporin Nanoparticles (Capsorine I.V.) Following Intravenous Administration Comparison with Sandimmune I.V. (Currently Marketed Formulation by Sandoz)

Nanoparticles of cyclosporine (Capsorine I.V.) prepared as described above (Examples 22 and 23) were reconstituted in saline and administered to a first group of 3 Sprague Dawley rats by intravenous bolus. A second group of 3 rats were given Sandimmune I.V., which contains Cremaphor/Ethanol after dilution in saline. Each group received the same dose of 2.5 mg/kg. Blood samples were taken at times 0, 5, 15, 30 (minutes) 1, 2, 4, 8, 24, 36 and 48 (hours). Levels of cyclosporine in the blood were assayed by HPLC and typical PK parameters were determined. The PK curves showed typical decay over time as follows:

|                | Decay Over Time |             |
|----------------|-----------------|-------------|
|                | AUC, mg-hr/ml   | Cmax, ng/ml |
| Capsorine I.V. | 12,228          | 2,853       |
| Sandimmune I.V.| 7,791           | 2,606       |

In addition, due to toxicity of the Sandimmune I.V. formulation, 2 of 3 rats in that group died within 4 hours after dosing. Thus the nanoparticle formulation (Capsorine I.V.) according to the present invention shows a greater AUC and no toxicity compared to the commercially available formulation (Sandimmune I.V.).

EXAMPLE 26

Pharmacokinetic (PK) Data for Cyclosporine Nanodroplets (Capsorine Oral) Following Oral Administration Comparison with Neoral (Currently Marketed Formulation by Sandoz)

Nanodroplets of cyclosporine prepared above were administered in orange juice, to a first group of 3 Sprague Dawley rats by oral gavage. A second group of 3 rats were given Neoral, a commercially available microemulsion formulation containing emulsifiers, after dilution in orange juice, also by oral gavage. Each group received the same dose of 12 mg/kg in an identical volume of orange juice. Blood samples were taken at times 0, 5, 15, 30 (minutes) 1, 2, 4, 8, 24, 36 and 48 (hours). Levels of cyclosporine in the blood were assayed by HPLC and typical PK parameters were determined. The PK curves showed typical decay over time as follows:

|                | Decay Over Time |             |
|----------------|-----------------|-------------|
|                | AUC, mg-hr/ml   | Cmax, ng/ml |
| Capsorine Oral | 3,195           | 887         |
| Neoral         | 3,213           | 690         |

Thus, the nanodroplet formulation (Capsorine Oral) of the present invention shows a similar PK behavior to the commercially available formulation (Neoral).

EXAMPLE 27

Intravenous Administration of Invention Paclitaxel Formulation (Capxol™) in Human Subjects In a Phase I clinical study, an invention formulation of paclitaxel (Capxol™) was administered by intravenous injection to 17 human subjects exhibiting advanced metastasis (Of the 17 subjects enrolled in the Phase I clinical study, 6 subjects had malignant melanoma and the remaining 11 subjects had metastatic breast cancer). The initial dose level (paclitaxel single dose) administered to each subject was 135 mg/m$^2$, and the subsequent doses were escalated to the next higher paclitaxel single dose level (per conventional paclitaxel dose regimen) if there were no significant adverse effects in the subject.

The maximum single dose administered was 375 mg/m$^2$ paclitaxel, with this dose being given in saline over a period of 30 minutes or less. This maximum single dose is significantly higher than the approved dose of paclitaxel (175 mg/m$^2$) administered as part of the conventional formulation, Taxol™.

No significant adverse events were noted in these subjects at this 375 mg/m$^2$ dose level, except for a small number of patients who exhibited some neurotoxicity (neuropathy). Accordingly, administration in invention formulations of paclitaxel at single dose levels which are as high as 500 mg/m$^2$, 1000 mg/m$^2$, 1500 mg/m$^2$, or 2000 mg/m$^2$ or higher, and which are less than the level at which 50% or more of the patients receiving this formulation exhibit a significant adverse event (e.g., a dose limiting toxicity), are contemplated.

One of the dose limiting toxicities in the administration of paclitaxel as part of the conventional formulation, Taxol™, is the neurotoxicity (neuropathy) of Taxol™, which is seen in up to 70% of patients receiving Taxol™. Surprisingly, an invention formulation of paclitaxel (Capxol™) shows significantly reduced incidence of neurotoxicity (neuropathy) even when utilizing higher paclitaxel dose levels than are permitted with Taxol™.

Another significant dose limiting toxicity for Taxol™ is myelosuppression, which is seen in up to 90% of patients receiving Taxol™ at a dose of 175 mg/m$^2$ (i.e., subject's neutrophil count drops to <2000/mm$^3$). As evidenced by white blood cell (WBC) and platelet counts, invention formulations of paclitaxel (Capxol™) are surprisingly found to be significantly less myelotoxic than Taxol™, even for patients receiving a much higher paclitaxel dose in accordance with the present invention, i.e., up to 375 mg/m$^2$.

Two of the malignant melanoma subjects being treated with the invention formulations of paclitaxel (Capxol™) did not exhibit any progression of the malignant melanoma for periods ranging from more than 15 weeks to more than 30 weeks. It is surprising that administration of the invention formulations of paclitaxel (Capxol™) generates a response in these patients because paclitaxel, administered in the conventional formulation of Taxol™, previously had not been found to generate a significant response in the treatment of malignant melanoma.

At least 2 of the 11 metastatic breast cancer subjects had a definitive response with administration of the invention formulations of paclitaxel (Capxol™). Two of the 11 metastatic breast cancer subjects were taken off the study due to progression of the disease, and the rest maintained stable disease at the time of evaluation. Thus, the invention formulations of paclitaxel (Capxol™) showed definite benefit to these cancer subjects.

Pharmacokinetic data in these patients showed an increase in the area under the curve (AUC) (e.g., amount of drug retained in patient's blood over time) with increasing dose. Therapeutic levels of the drug (>50 ng/ml) were maintained in whole blood up to 48 hours after dosing.

In one patient with breast cancer who had severe psoriasis over the trunk and limbs, it was surprisingly noted that her psoriasis was significantly reduced after administration of the first course of treatment of the invention formulation (Capxol™). The psoriasis remained in control over the next several courses of treatment of the invention formulation (Capxol™), indicating that paclitaxel (administered as Capxol™) can have a positive effect in the treatment of psoriasis. Thus, paclitaxel (administered as Capxol™) can be useful in the treatment of psoriasis and other proliferative diseases (e.g., multiple sclerosis, vascular restinosis, and the like).

EXAMPLE 28

Intraarterial Administration of Invention Paclitaxel Formulation (Capxol™) in Human Subjects In a further Phase I clinical study, an invention formulation of paclitaxel (Capxol™) was administered intra-arterially to more than 25 patients exhibiting primary and/or secondary liver tumors and/or solid tumors with local-regional involvement. The clinical study protocol called for administration of the invention formulation of paclitaxel (Capxol™) by intra-arterial injection (chemo-embolization) into the artery feeding the tumor that was to be treated. For example in patients with hepatic disease, the hepatic artery could be catheterized and the drug injected directly into the artery feeding the tumor.

Starting with a dose of 90 mg of paclitaxel per patient in the initial course of treatment, the dose was escalated for subsequent courses of treatment to over 300 mg per patient. Tumor response to this course of treatment in these patients was assessed by X-ray, MRI, CT scan and/or angiography.

The treated patients included patients with hepatocellular carcinoma, multifocal hepatoma, metastatic breast cancer, prostatic cancer, pancreatic cancer, non-small cell lung cancer (squamous cell cancer), colon cancer, renal cancer, intestinal sarcoma, esophageal cancer, melanoma, ependymoma, and head & neck cancer. Surprisingly, responses to treatment (e.g., reductions in cancer size, and the like) were observed for most of these patients, including patients with lung cancer, prostatic cancer, breast cancer, and/or hepatic disease. In general, intra-arterial injection was remarkably well tolerated by the treated patients, as toxicity in these patients was very limited. Late toxicity included slight alopecia, a slight reduction in WBC and a sense of fatigue lasting 4–5 days.

It is to be noted that intra-arterial injection of the invention formulation (Capxol) of paclitaxel allowed the administration of the drug substance paclitaxel in a manner not previously possible. Previously only a very limited dose of paclitaxel could be administered intra-arterially due to the low solubility of paclitaxel. The invention formulation allows intra-arterial administration at much higher doses thereby allowing a more efficacious treatment of the disease. Furthermore, this mode of treatment results in responses to cancers e.g., prostatic and pancreatic cancer which are normally considered nonresponsive.

EXAMPLE 29

Treatment of Diseases with Invention Paclitaxel Formulation (Capxol™) where Use of Steroids is Contraindicated Little progress has been made in the development of treatment regimens which are effective to reduce and/or inhibit progression of metastatic melanoma following conventional chemotherapy in patients who have this disease. Interferon and interleukin have been utilized alone or in combination for such treatment. Unfortunately, the response rate (i.e., the percentage of patients exhibiting a positive treatment response (e.g., reduction and/or inhibition of the progression of metastatic melanoma following conventional chemotherapy) after administration of the drug) is less than 25%. Similarly, paclitaxel (administered in its currently approved formulation, Taxol™) has been evaluated for efficacy against metastatic melanoma, and has been shown to have definite but modest activity with a response rate of 15%. Further, the response rate utilizing interleukin-2 (IL-2) is similar, but, unlike complete responses (CRs) induced by single cytotoxic agents, CRs induced by IL-2, although uncommon, can be durable.

The combination of paclitaxel (administered in its conventional, approved formulation, Taxol™) and IL-2 has not previously been evaluated for treatment of metastatic melanoma because of the requirement for corticosteroid premedication prior to administration of Taxol™. Corticosteroid premedication is required to prevent anaphylactic-like hypersensitivity reactions associated with the cremophor vehicle of Taxol™. The corticosteroids introduced due to this requirement cause lysis of LAK cells, resulting in the loss of any benefit from administration of IL-2.Thus, Taxol™ cannot be used in combination with drugs like IL-2 or interferon.

The invention formulations of paclitaxel (e.g., Capxol™) are cremophor-free formulations of paclitaxel which are freely dispersible in aqueous media. Because the invention formulations are cremophor-free, the risk of hypersensitivity reactions on administration of the invention formulations is remote. Thus, corticosteroid premedication is not required with administration of invention formulations of paclitaxel (e.g., Capxol™). This discovery permits treatment of patients in need thereof with a combination of paclitaxel (Capxol™) and IL-2 (e.g., metastatic melanoma patients who have failed conventional chemotherapy, patients with renal cell carcinoma, and the like).

For example, metastatic melanoma patients who have failed conventional chemotherapy can be treated with a combination of paclitaxel (Capxol™) and IL-2. Dosing of these patients can be accomplished by the following regimen. An invention formulation of paclitaxel (e.g., Capxol™) is administered intravenously over approximately 30 minutes at an initial dose of 200 mg/m$^2$ on day 1 (before start of IL-2 dosing) and at a dose of 100 mg/m$^2$ on day 6 (upon completion of IL-2 dosing). IL-2 is administered intravenously at 18 MIU/m$^2$ over 6 hours beginning after administration of the initial dose of paclitaxel, followed by 18 MIU/m$^2$ administered intravenously over 12 hours, followed by 18 MIU/m$^2$ administered intravenously over 24 hours, followed by 4.5 MIU/m 2/day administered intravenously over 3 consecutive days, with the total administration time of IL-2 being 120 hours from day 1 to day 6. Other suitable schedules for drug administration reported in the literature can also be utilized.

As a further example, patients with renal cell carcinoma can be treated with a combination of paclitaxel (e.g., Capxol™) and IL-2. Conventionally, IL-2 is used for the treatment of these patients. However, paclitaxel (administered in its approved formulation, Taxol™) cannot be administered to these patients, alone or in combination with IL-2, because of the need for corticosteroid premedication prior to administration of Taxol™, as discussed above. But, as discussed above, invention formulations of paclitaxel (e.g., Capxol™) do not require corticosteroid premedication, and therefore are suitable for administration in combination chemotherapy with IL-2 for the treatment of these patients.

Generalizing the foregoing exemplary combination therapeutic treatments of specific diseases, any situation requiring treatment of patients utilizing IL-2, interferon or other cytokine biochemotherapy agents is also suitable for the treatment of these patients utilizing invention formulations of taxanes (e.g., paclitaxel, docetaxel, and like taxanes which require steroid premedication) in combination therapy with the cytokine biochemotherapy. Further, in any situation where treatment of a disease with taxanes (e.g., paclitaxel (in its approved formulation Taxol™), docetaxel (in its approved formulation Taxotere™), and other taxanes which require steroid premedication) is desirable in conjunction with biochemotherapy agents (e.g., interleukins, interferons, other cytokines, and the like), use of invention formulation of taxanes obviates the need for steroid administration and makes possible the treatment of patients with combination chemotherapy. This combination chemotherapy can provide added benefits to the treated patient.

This example demonstrates how the use of invention formulations is possible in any situation where steroid medication is contraindicated.

EXAMPLE 30

Administration of Taxanes (e.g., Paclitaxel) without Premedication or GSF-support Hypersensitivity reactions are a problem associated with administration of paclitaxel (in its commercially available formulation, Taxol™), docetaxel (in its commercially available formulation, Taxotere™), and other taxanes.

Taxol™, the commercially available formulation of the anti-cancer agent paclitaxel, is available as a drug which can be dissolved prior to administration utilizing cremophor (polyethoxylated castor oil) as a surfactant and ethanol as a vehicle. Hypersensitivity reactions (e.g., due to drug- and/or vehicle-induced toxicity) to Taxol™ occur in about 40% of all patients receiving Taxol™. Because of this documented hypersensitivity reaction, all patients to whom Taxol™ is to be administered are required to take premedication that comprises corticosteroids and antihistamines prior to receiving Taxol™.

Similarly, Taxotere™, the commercially available formulation of the anti-cancer agent docetaxel, is another taxane that is dissolved in the surfactant Tween-80. Because of analogous hypersensitivity reactions, administration of Taxotere™ also requires steroid premedication.

Surprisingly, the invention formulations of taxanes (e.g., Capxol™ (which comprises nanoparticles of paclitaxel stabilized by human serum albumin), and the like) were found surprisingly to not induce any hypersensitivity reactions in human patients. As a result, patients receiving the invention formulations of taxanes (e.g., paclitaxel (in Capxol™ formulation), docetaxel, and the like) need not be premedicated with steroids.

Like hypersensitivity reactions, myelosuppression is a problem (i.e., a dose limiting toxicity) associated with administration of paclitaxel in its commercially available formulation, Taxol™.

A large number of patients receiving Taxol™ are required to take G-CSF support to prevent excessive myelosuppression. For example, in those patients receiving Taxol™ without G-CSF support, the neutrophil counts or absolute granulocyte counts may drop to dangerously low levels (i.e., less than about 500/mm$^3$).

Thus, it was surprisingly found that the degree of myelosuppression in patients receiving the invention formulation of paclitaxel (e.g., Capxol™) is much lower than for patients receiving the same dose of paclitaxel in the commercially available formulation of paclitaxel, Taxol™. Unlike patients receiving Taxol™, patients receiving invention formulations of paclitaxel (e.g., Capxol™), even at doses as high as 375 mg/m$^2$, exhibit little myelosuppression, and require no G-CSF support. Accordingly, it can be surprisingly noted that patients receiving invention formulations of taxanes (e.g., paclitaxel, docetaxel, and the like) do not require cytokine (e.g., G-CSF, and the like) support or any other means of support required to avoid excessive myelosuppression.

EXAMPLE 31

Localized Treatment of Brain Tumors and Tumors within the Peritoneum

Delivering pharmacologically active agents (e.g., antiinfectives, immunosuppressives, chemotherapeutic agents, and the like) locally to a specific treatment site (e.g., localized tumor site, and the like) is an effective method for long term exposure to the drug while minimizing dose limiting side effects. The biocompatible materials discussed above can be employed in several physical forms (e.g., gels (crosslinked or uncrosslinked), and the like) for the purpose of facilitating this controlled local delivery. When so utilized, these biocompatible materials provide matrices from which pharmacologically active agent(s) (e.g., taxanes (paclitaxel, docetaxel, and the like), and the like) can be locally released and/or dispersed (e.g., at the site of the solid tumor (e.g., brain (brain cancer), peritoneum (ovarian cancer), and the like), and the like) by diffusion across and/or degradation of the matrix.

Thus, the invention formulations of paclitaxel (e.g., Capxol™) can be dispersed within a matrix of the biocompatible material(s) discussed above. This matrix provides a sustained release formulation of paclitaxel for the treatment of brain tumors and tumors within the peritoneal cavity (e.g., ovarian cancer, metastatic diseases, and the like). When temperature sensitive materials are utilized in the formation of this matrix, the invention formulations of paclitaxel (e.g., Capxol™) can be injected in a liquid formulation of the temperature sensitive materials which gels at the tumor site and provides for slow release of Capxol™.

Capxol™ (an invention formulation of paclitaxel) was reconstituted in a 1% solution of sodium alginate. The solution was then pumped through a device to make gel beads of the Capxol™/alginate solution in aqueous calcium chloride.

Some beads containing Capxol™ were separated from the solution and placed in culture media. The release of paclitaxel from the beads containing Capxol™ into the media was measured over time at 37° C. It was found that sustained release of paclitaxel could be obtained from the beads containing Capxol™ for periods of up to 28 days.

Additional beads containing Capxol™ were separated from the solution and implanted into the peritoneal cavity of rats to determine release of paclitaxel from within the beads. The rats were sacrificed 2 weeks later and the gelled beads retrieved. Measurement of paclitaxel within the beads showed that most of the drug had been released into the peritoneal cavity of the rats.

EXAMPLE 32

Reduction of Dosing Cycle Time and Increase in Dose Levels in Administration of Taxanes Due to the low toxicity of invention formulations of paclitaxel (or other pharmacologically active agents, e.g., docetaxel (commercially available as Taxotere™), and the like), it is possible to reduce the associated cycle time (i.e., the time between consecutive administrations of doses of the pharmacologically active agent) and/or increase the associated dose levels (i.e., the amount of each dose of pharmacologically active agent).

In the case of paclitaxel administered in its approved formulation, Taxol™, or docetaxel administered in its approved formulation, Taxotere™, the typical cycle time is 3 weeks. However, invention formulations of the taxane (e.g., paclitaxel, docetaxel, and the like) can be administered with cycle times in the range of from about 1 day to about 3 weeks or more, with a preferable cycle time of about 3 to about 15 days, as required to provide maximum benefit from treatment to the patient in need thereof. For example, doses of 25–250 mg/m$^2$ of paclitaxel in invention formulations can be administered every 1–20 days in patients suffering from any disease in which treatment with paclitaxel shows some benefit.

In the case of paclitaxel administered in its approved formulation, Taxol™, the typical dose level is 100–135 mg/m$^2$ with a cycle time of 1 week. However, invention formulations of the taxane (e.g., paclitaxel, docetaxel, and the like) can be administered with this same cycle time in doses which exceed typical dose levels (e.g., doses greater than 135 mg/m$^2$ and up to 400 mg/m$^2$ or greater, as required to treat patients suffering from any disease in which treatment with a taxane shows some benefit.

EXAMPLE 33

Oral Administration of Taxanes

Oral administration of taxanes (e.g., paclitaxel, docetaxel, and the like) has historically been challenging.

However, it has been discovered that invention formulations of a taxane (e.g., paclitaxel, docetaxel, and the like) can be administered orally in combination with oral cyclosporin and/or oral FK506 (i.e., tacrolimus).

Invention formulation(s) of the taxane and/or cyclosporin and/or FK506 can be prepared in accordance with the invention methods. These formulation(s) can be prepared as separate formulations (for oral administration in series), or as a combination formulation comprising the taxane and at least one of cyclosporin and FK506 (for oral administration in parallel).

Once these formulation(s) have been prepared, they can be administered to a patient suffering from any disease in which treatment with a taxane shows some benefit, utilizing various dose amounts and cycle times necessary to effect treatment of the disease.

Without limiting the scope of this example, the oral administration of the taxane formulation is believed to be facilitated by the oral administration (either in parallel (i.e., concurrent with administration of the taxane formulation) or in series (i.e., prior to administration of the taxane formulation)) of cyclosporin and/or FK506. Cyclosporin and/or FK506 are believed to inhibit the function of P-glycoprotein efflux pumps on intestinal cells. Uninhibited, these P-glycoprotein efflux pumps would likely pump any absorbed paclitaxel formulation out of its associated intestinal cell.

While the invention has been described in detail with reference to certain preferred embodiments thereof, it will be understood that modifications and variations are within the spirit and scope of that which is described and claimed.

That which is claimed is:

1. A drug delivery system comprising particles of a solid or liquid, substantially water insoluble pharmacologically active agent, coated with protein,
    wherein said protein coating has free protein associated therewith,
    wherein a portion of said pharmacologically active agent is contained within said protein coating and a portion of said pharmacologically active agent is associated with said free protein, and
    wherein the average diameter of said particles is no greater than about 1 micron.

2. A drug delivery system according to claim 1 wherein the average diameter of said particles is less than 200 nm.

3. A drug delivery system according to claim 2 wherein said system is sterile filtered.

4. A drug delivery system according to claim 1 wherein said particles are amorphous, crystalline, or a mixture thereof.

5. A drug delivery system according to claim 4 wherein said particles are substantially amorphous.

6. A drug delivery system according to claim 1 wherein said particles are suspended in a biocompatible aqueous liquid.

7. Bioprotected particles of a substantially water insoluble pharmacologically active agent coated with protein,
    wherein said particles are surrounded by free protein associated therewith,
    wherein a portion of said pharmacologically active agent is contained within said protein coating and a portion of said pharmacologically active agent is associated with said free protein surrounding said protein coating, and
    wherein the average diameter of said particles is no greater than about 1 micron.

8. Bioprotected particles according to claim 7 wherein the average diameter of said particles is less than 200 nm.

9. Bioprotected particles according to claim 8 wherein said particles are sterile filtered.

10. Bioprotected particles according to claim 7 wherein said particles are amorphous, crystalline, or a mixture thereof.

11. Bioprotected particles according to claim 10 wherein said particles are substantially amorphous.

12. Bioprotected particles according to claim 7 wherein said pharmacologically active agent is paclitaxel and said protein is albumin.

13. A drug delivery system according to claim 1 wherein said pharmacologically active agent is selected from the group consisting of an anti-neoplastic, an anesthetic and a hormone.

14. A drug delivery system according to claim 13 wherein said anti-neoplastic is a taxane.

15. A drug delivery system according to claim 13 wherein said anesthetic is propofol.

16. A drug delivery system according to claim 13 wherein said hormone is a thyroid hormone.

17. A drug delivery system according to claim 1 wherein said pharmacologically active agent is non-crystalline.

18. The bioprotected particles according to claim 7 wherein said pharmacologically active agent is selected from the group consisting of an anti-neoplastic, an anesthetic and a hormone.

19. The bioprotected particles according to claim 18 wherein said anti-neoplastic is a taxane.

20. The bioprotected particles according to claim 18 wherein said anesthetic is propofol.

21. The bioprotected particles according to claim 18 wherein said hormone is a thyroid hormone.

* * * * *